US012577552B2

(12) United States Patent
Claar et al.

(10) Patent No.: US 12,577,552 B2
(45) Date of Patent: Mar. 17, 2026

(54) FACTOR IX VARIANTS AND USES THEREOF IN THERAPY

(71) Applicant: CSL INNOVATION PTY LTD, Melbourne (AU)

(72) Inventors: Philipp Claar, Marburg (DE); Thomas Weimer, Gladenbach (DE); Walid Azar, Melbourne (AU); Holger Lind, Marburg (DE); Marco Hofmann, Lahntal (DE)

(73) Assignee: CSL Innovation Pty Ltd, Melbourne (AU)

( * ) Notice: Subject to any disclaimer, the term of this patent is extended or adjusted under 35 U.S.C. 154(b) by 1141 days.

(21) Appl. No.: 17/440,281

(22) PCT Filed: Mar. 18, 2020

(86) PCT No.: PCT/EP2020/057400
§ 371 (c)(1),
(2) Date: Sep. 17, 2021

(87) PCT Pub. No.: WO2020/187969
PCT Pub. Date: Sep. 24, 2020

(65) Prior Publication Data
US 2022/0154161 A1 May 19, 2022

(30) Foreign Application Priority Data
Mar. 19, 2019 (EP) .................................... 19163619

(51) Int. Cl.
*C12N 9/64* (2006.01)
*A61K 38/48* (2006.01)

(52) U.S. Cl.
CPC .......... *C12N 9/644* (2013.01); *A61K 38/4846* (2013.01); *C12Y 304/21022* (2013.01)

(58) Field of Classification Search
CPC ................ C12N 9/644; A61K 38/4846; C12Y 304/21022
See application file for complete search history.

(56) References Cited

U.S. PATENT DOCUMENTS

| | | | |
|---|---|---|---|
| 6,531,298 B2 * | 3/2003 | Stafford ......... | C12Y 304/21022 435/69.6 |
| 2008/0102115 A1 * | 5/2008 | Oyhenart ............... | C12N 9/644 424/463 |
| 2014/0322191 A1 * | 10/2014 | Madison ................. | C12N 9/644 424/94.64 |
| 2016/0346366 A1 * | 12/2016 | Jacobs ........... | C12Y 304/21022 |
| 2024/0293516 A1 * | 9/2024 | Pestel ..................... | A61K 38/36 |

FOREIGN PATENT DOCUMENTS

| | | |
|---|---|---|
| KR | 10-2017-0054545 A | 5/2017 |
| WO | WO 2005/001025 A2 | 1/2005 |
| WO | WO 2005/024044 A2 | 3/2005 |
| WO | WO 2005/055950 A2 | 6/2005 |
| WO | WO 2006/127896 A2 | 5/2006 |
| WO | WO 2007/144173 A1 | 12/2007 |
| WO | WO 2007/149406 A2 | 12/2007 |
| WO | WO 2010/012451 A1 | 2/2010 |
| WO | WO 2011/004361 A2 | 1/2011 |
| WO | WO 2012/006624 A2 | 1/2012 |
| WO | WO 2012061654 A1 | 5/2012 |
| WO | WO 2015/106052 A1 | 7/2015 |
| WO | WO 2017/024060 A1 | 2/2017 |
| WO | WO 2018/022844 A2 | 2/2018 |
| WO | WO 2018/217731 A1 | 11/2018 |
| WO | WO 2019/020966 A1 | 1/2019 |

OTHER PUBLICATIONS

Smith, Temple F. et al., "Comparison of Biosequences," Advances in Applied Mathematics, vol. 2, pp. 482-489 (1981).
Beattie, Wanda G. et al., "Structure and evolution of human α-fetoprotein deduced from partial sequence of cloned cDNA," Gene., vol. 20, pp. 415-422 (1982).
Cooke, Nancy E. et al., "Serum Vitamin D-binding Protein is a Third Member of the Albumin and Alpha Fetoprotein Gene Family," J. Clin. Invest., vol. 76, pp. 2420-2424 (1985).
Fares, Faud A. et al., "Design of a long-acting follitropin agonist by fusing the C-terminal sequence of the chorionic gonadotropin β subunit to the follitropin β subunit," Proc. Natl. Acad. Sci., vol. 89, pp. 4304-4308 (1992).
Lichenstein, Henry S. et al., "Afamin Is a New Member of the Albumin, α-Fetoprotein, and Vitamin D-binding Protein Gene Family," The Journal of Biological Chemistry, vol. 269, No. 27, pp. 18149-18154 (1994).
Defrees, Shawn et al., "GlycoPEGylation of recombinant therapeutic proteins produced in *Escherichia coli*," Glycobiology, vol. 16, No. 9, pp. 833-843 (2006).
Schellenberger, Volker et al., "A recombinant polypeptide extends the in vivo half-life of peptides and proteins in a tunable manner," Nature Biotechnology, vol. 27, No. 12, 1186-1190, including two pages of online methods (2009).
Simioni, Paolo, M.D., Ph.D., et al., "X-Linked Thrombophilia with a Mutant Factor IX (Factor IX Padua)," The New England Journal of Medicine, vol. 361, pp. 1671-1675 (2009).
Peters, Robert T. et al., "Prolonged Activity of Factor IX as a Monomeric Fc Fusion Protein," Blood, vol. 115, No. 10, pp. 2057-2064 (2010).

(Continued)

*Primary Examiner* — Sharmila G Landau
*Assistant Examiner* — Lioubov G Korotchkina
(74) *Attorney, Agent, or Firm* — Finnegan, Henderson, Farabow, Garrett & Dunner, LLP

(57) ABSTRACT

This invention provides Factor IX variants, molecules comprising the variants, nucleic acids encoding the variants, compositions comprising the variants or the nucleic acids encoding the variants, and their use in methods for the modulation of hemostasis, for example in the prophylaxis or treatment of hemophilia B. The Factor IX variants have improved biological properties relative to other Factor IX variants and/or relative to wild-type Factor IX.

11 Claims, No Drawings

Specification includes a Sequence Listing.

(56) References Cited

OTHER PUBLICATIONS

Shapiro, Amy D. et al., "Recombinant factor IX-Fc fusion protein (rFIXFc) demonstrates safety and prolonged activity in a phase 1/2a study in hemophilia B patients," Blood, vol. 119, pp. 666-672 (2012).

Anguela, Xavier M. et al., "Robust ZFN-mediated genome editing in adult hemophilic mice," Blood, vol. 122, No. 19, pp. 3283-3287 (2013).

Kao, Chung-Yang et al., "Incorporation of the factor IX Padua mutation into FIX-Triple improves clotting activity in vitro and in vivo," Thrombosis and Haemostasis, vol. 110, pp. 244-256 (2013).

Powell, Jerry S., M.D. et al., "Phase 3 Study of Recombinant Factor IX Fc Fusion Protein in Hemophilia B," The New England Journal of Medicine, vol. 369. No. 24, pp. 2313-2323 (2013).

Collins, Peter W. et al., "Recombinant long-acting glycoPEGylated factor IX in hemophilia B: a multinational randomized phase 3 trial," Blood, vol. 24, No. 26, pp. 3880-3886 (2014).

Barzel, A. et al., "Promoterless gene targeting without nucleases ameliorates haemophilia B in mice," Nature, vol. 517, pp. 360-374 (2015).

Calo, Doron et al., "Enhancing the longevity and in vivo potency of therapeutic proteins: The power of CTP," Precision Medicine, 2: e989, pp. 1-8 (2015).

Perot, Eloïse et al., "Expression and characterization of a novel human recombinant factor IX molecule with enhanced in vitro and in vivo clotting activity," Thrombosis Research, vol. 135, pp. 1017-1024 (2015).

Sharma, Rajiv et al., "In vivo genome editing of the albumin locus as a platform for protein replacement therapy," Blood, vol. 126, No. 15, pp. 1777-1784 (2015).

Wang, Qiang M.D. et al., "In Vivo CRISPR/Cas9-Targeted Genome Editing Recovers Factor IX Expression Restoring Haemostasis in a Mouse Model," Blood, vol. 130 (Supplement 1): 5562, two (2) pages (2017).

Samelson-Jones, Benjamin J. et al., "Protein-Engineered Coagulation Factors for Hemophilia Gene Therapy," Molecular Therapy: Methods & Clinical Development, vol. 12, pp. 184-201 (2018).

International Search Report and Written Opinion for International Application No. PCT/EP2020/057400, dated Apr. 15, 2020 (14 pages).

* cited by examiner

FACTOR IX VARIANTS AND USES THEREOF IN THERAPY

This application is a national stage filing under 35 U.S.C. § 371 of International Application No. PCT/EP2020/ 057400, filed on Mar. 18, 2020, which claims priority to European Patent Application No. 19163619.0, filed Mar. 19, 2019. The contents of these applications are each incorporated herein by reference.

TECHNICAL FIELD

This invention relates to Factor IX variants, molecules encoding the variants, nucleic acids encoding the variants, compositions comprising the variants or the nucleic acids encoding the variants, and their use in methods for the modulation of hemostasis, for example in the treatment or prophylaxis of a blood coagulation disorder such as hemophilia B.

BACKGROUND

Human coagulation Factor IX (FIX) is a key component in the coagulation cascade. Certain loss-of-function alterations in the gene encoding Factor IX cause Factor IX deficiency, leading to the bleeding disorder hemophilia B (also known as Christmas disease), which generally requires Factor IX replacement therapy.

Factor IX is a single-chain glycopolypeptide with a molecular weight of 57 kDa. It is synthesised in the liver and secreted into the blood stream after cleavage of a 46-amino acid (aa) prepropeptide. Factor IX circulates in the blood stream as an inactive zymogen of 415 amino acids. It contains the N-terminal Gla domain, followed by two epidermal growth factor (EGF) domains, an activation peptide, and a trypsin-type serine protease domain at the C-terminus. Upon vascular damage, Factor IX is converted to its active form, Factor IXa, by proteolysis of a 35-aa activation peptide at R145-A146 and R180-V181, leading to the formation of two polypeptide chains, an N-terminal light chain (aa 1-145; 18 kDa) and a C-terminal heavy chain (aa 181-415; 28 kDa), which are held together by a disulphide bridge. The role of this activated factor IX in the blood coagulation cascade is to activate Factor X to its active form (Factor Xa) through interactions with $Ca^{2+}$ ions, membrane phospholipids, and Factor Villa. Factor Xa cleaves prothrombin, which yields active thrombin. Thrombin converts fibrinogen to fibrin, which cross-links to form the blood clot.

Hemophilia B is caused by non-functional or missing Factor IX and generally requires Factor IX replacement therapy, such as Factor IX concentrates from plasma or recombinant forms of Factor IX. Although effective, some of the current Factor IX replacement therapies suffer from the short half-life of the Factor IX polypeptides administered, therefore requiring frequent intravenous injections at high doses. Furthermore, large amounts of Factor IX polypeptide are required for protein replacement, which can be costly. Therefore, there is a need for Factor IX polypeptide with improved biological properties. Specifically, it is desirable to reduce the amount of Factor IX polypeptide that is required to achieve the necessary levels of Factor IX activity. It is also desirable to reduce the frequency of administrations, i.e. to increase the time period between the administrations.

The present inventors have found that Factor IX variants having substitutions at certain amino acid positions relative to the amino acids in those positions in the wild-type Factor IX polypeptide may have advantageous properties, which makes them particularly suitable in the treatment or prophylaxis of bleeding disorders such as hemophilia B. For example, the Factor IX variants of the present invention may have higher pro-coagulant activity ('specific activity') compared to the wild-type Factor IX polypeptide, and even compared to other known Factor IX variants. The higher specific activity may be advantageous in prophylaxis and/or therapy because less total Factor IX polypeptide is required to be administered to achieve the same level of Factor IX activity as with wild-type Factor IX or with other Factor IX variants that have a lower specific activity. The higher specific activity may also be advantageous because it allows for a quicker therapeutic response (e.g., when treating an acute bleeding episode). Furthermore, Factor IX variants with a higher specific activity may be particularly useful in gene therapy approaches, e.g. because they could allow the administration of lower viral vector doses and thereby reduce or avoid the anti-vector immune response that is seen in some subjects (e.g. anti-capsid cellular immunity), whilst still providing clinically significant levels of Factor IX activity.

The present inventors have furthermore shown that the Factor IX variants of the invention may be linked (e.g. via a cleavable linker) to half-life enhancers while maintaining the capability for increased Factor IX activity. Such Factor IX variants may therefore have both a longer functional half-life in vivo as well as a higher pro-coagulant activity once activated. This may be particularly advantageous because less total Factor IX polypeptide is required to achieve the same level of Factor IX activity as with wild-type Factor IX or with other Factor IX variants, and additionally less frequent administrations are required (because each administration provides Factor IX polypeptide with increased Factor IX activity for a longer period of time).

DISCLOSURE OF THE INVENTION

The present invention provides Factor IX variants with improved biological properties relative to other Factor IX variants and/or relative to wild-type Factor IX. In particular, the Factor IX variants as described herein may have greater coagulation activity (greater specific activity) relative to wild-type Factor IX, and/or relative to other Factor IX variants. The invention also provides molecules comprising a Factor IX variant linked to a half-life enhancer which provides the Factor IX variant with a longer functional half-life in vivo. The Factor IX variants of the invention and molecules comprising the same are therefore particularly useful in the prevention or treatment of bleeding disorders such as hemophilia B. The Factor IX variant or a molecule comprising the same is typically a recombinant polypeptide.

In one aspect, the invention therefore provides a molecule comprising a Factor IX variant polypeptide comprising the amino acid H (histidine) at a position corresponding to position 410 of wild-type Factor IX, or comprising an amino acid other than R (arginine) at a position corresponding to position 338 of wild-type Factor IX. The invention therefore provides, for example, a molecule comprising the amino acid V (valine), T (threonine) or W (tryptophan), e.g. V or T, in particular V, at a position corresponding to position 338 of wild-type Factor IX. It will be understood by those skilled in the art that the term "amino acid" in the context of a polypeptide is used interchangeably with "amino acid residue".

The numbering refers to the amino acid positions in the wild-type Factor IX as identified in SEQ ID NO: 1. For example, "a molecule comprising a Factor IX variant polypeptide comprising the amino acid H at a position corresponding to position 410 of wild-type Factor IX" refers to a molecule comprising a Factor IX variant polypeptide which comprises the amino acid H at a position that corresponds to position 410 of SEQ ID NO: 1 (which has the amino acid E at that position), e.g. the Factor IX variant polypeptide comprises the amino acid H in position 410 of SEQ ID NO: 1. Another way of indicating this feature is e.g. "410H", or "E410H".

The invention also provides a molecule comprising a Factor IX variant polypeptide comprising the amino acid H at a position corresponding to position 410 of wild-type Factor IX, and comprising an amino acid other than R at a position corresponding to position 338 of wild-type Factor IX.

The amino acid at a position corresponding to position 338 of wild-type Factor IX may be any amino acid that increases the specific activity of the Factor IX variant polypeptide relative to a Factor IX polypeptide having the same sequence with the amino acid R at position 338. The specific activity is typically determined using an in vitro one-stage clotting assay, e.g. an aPTT assay, and other methods are known to the skilled person in the art. In a preferred embodiment Factor IX activity is determined using an in vitro aPTT-based one stage clotting assay, typically as described in Example 3.

The relative specific activity of the Factor IX variant polypeptide may be increased by a factor of at least 3, or at least 4, relative to a Factor IX polypeptide having the same sequence with the amino acid R at position 338 (wherein in each polypeptide the amino acid corresponding to position 410 is E).

The relative specific activity of the Factor IX variant polypeptide may be increased by a factor of at least 2.5, at least 3.0, or at least 3.5, relative to a Factor IX polypeptide having the same sequence with the amino acid R at position 338 (wherein in each polypeptide the amino acid corresponding to position 410 is H).

The relative specific activity of the Factor IX variant polypeptide may be increased by a factor of at least 5, at least 6, or at least 7, when comparing a Factor IX variant polypeptide comprising the amino acid H at a position corresponding to position 410 of wild-type Factor IX and comprising an amino acid other than R at a position corresponding to position 338 of wild-type Factor IX, relative to a Factor IX polypeptide having the same sequence with the amino acid E at position 410 and the amino acid R at position 338. The relative specific activity of a Factor IX variant polypeptide comprising the amino acid H at a position corresponding to position 410 of wild-type Factor IX and comprising an amino acid other than R at a position corresponding to position 338 of wild-type Factor IX may therefore be increased by a factor of at least 5, at least 6, or at least 7 relative to wild-type Factor IX (e.g. SEQ ID NO: 1).

The relative specific activity of the Factor IX variant polypeptide may be increased by a factor of at least 1.5 when comparing a Factor IX variant polypeptide comprising the amino acid H at a position corresponding to position 410 of wild-type Factor IX and comprising an amino acid other than R at a position corresponding to position 338 of wild-type Factor IX, relative to each of (i) a Factor IX polypeptide having the same sequence with the amino acid H at position 410 and the amino acid R at position 338, and (ii) a Factor IX polypeptide having an the same sequence with the amino acid E at position 410 and the amino acid other than R at position 338.

In one embodiment, the molecule may therefore comprise the amino acid H at a position corresponding to position 410 of wild-type Factor IX, and an amino acid selected from the group consisting of V, T, W, L, Y or E, such as V, T, W or L, for example V, T or W, e.g. V or T, in particular V, at a position corresponding to position 338 of wild-type Factor IX.

In other embodiments, the amino acid at the position corresponding to position 338 of wild-type Factor IX is an amino acid other than R and L.

In an exemplary embodiment, the Factor IX variant polypeptide comprises the amino acid H at a position corresponding to position 410 of wild-type Factor IX and an amino acid selected from the group consisting of V, T and W at a position corresponding to position 338 of wild-type Factor IX.

In another embodiment, the Factor IX variant polypeptide comprises the amino acid H at a position corresponding to position 410 of wild-type Factor IX and an amino acid selected from the group consisting of V and T at a position corresponding to position 338 of wild-type Factor IX.

In a specific embodiment, the Factor IX variant polypeptide comprises the amino acid H at a position corresponding to position 410 of wild-type Factor IX and the amino acid V at a position corresponding to position 338 of wild-type Factor IX.

In a specific embodiment, the Factor IX variant polypeptide comprises the amino acid H at a position corresponding to position 410 of wild-type Factor IX and the amino acid T at a position corresponding to position 338 of wild-type Factor IX.

In a specific embodiment, the Factor IX variant polypeptide comprises the amino acid H at a position corresponding to position 410 of wild-type Factor IX and the amino acid W at a position corresponding to position 338 of wild-type Factor IX.

In some embodiments, the Factor IX variant polypeptide has an amino acid at the position(s) as described above, and it comprises an amino acid sequence having at least 70% sequence identity to SEQ ID NO: 1. In a specific embodiment, the Factor IX variant polypeptide comprises an amino acid sequence having at least 75%, at least 80%, at least 85%, at least 90%, at least 95%, at least 96%, at least 97%, at least 98%, or at least 99% sequence identity to SEQ ID NO: 1. In a particular embodiment, the Factor IX variant polypeptide comprises an amino acid sequence having at least 95% sequence identity to SEQ ID NO: 1. In any of these embodiments, the Factor IX variant polypeptide is biologically active, i.e. it is capable of activating Factor X (i.e. generating Factor Xa).

In particular, the Factor IX variant polypeptide may have an amino acid at the position(s) as described above, and it may have at least 70% sequence identity to SEQ ID NO: 1. In a specific embodiment, the Factor IX variant polypeptide has at least 75%, at least 80%, at least 85%, at least 90%, at least 95%, at least 96%, at least 97%, at least 98%, or at least 99% sequence identity to SEQ ID NO: 1. In a particular embodiment, the Factor IX variant polypeptide has at least 95% sequence identity to SEQ ID NO: 1. In any of these embodiments, the Factor IX variant polypeptide is biologically active, i.e. it is capable of activating Factor X (i.e. generating Factor Xa).

An exemplary embodiment therefore is a Factor IX variant polypeptide comprising the amino acid H at a position corresponding to position 410 of wild-type Factor IX and an amino acid selected from the group consisting of V, T and W (e.g. V or T, particularly V) at a position corresponding to position 338 of wild-type Factor IX, and wherein the Factor IX variant polypeptide comprises an amino acid sequence having at least 70% sequence identity to SEQ ID NO: 1.

Another exemplary embodiment is a Factor IX variant polypeptide comprising the amino acid H at a position corresponding to position 410 of wild-type Factor IX and an amino acid selected from the group consisting of V, T and W (e.g. V or T, particularly V) at a position corresponding to position 338 of wild-type Factor IX, and wherein the Factor IX variant polypeptide comprises an amino acid sequence having at least 80% sequence identity to SEQ ID NO: 1.

Another exemplary embodiment is a Factor IX variant polypeptide comprising the amino acid H at a position corresponding to position 410 of wild-type Factor IX and an amino acid selected from the group consisting of V, T and W (e.g. V or T, particularly V) at a position corresponding to position 338 of wild-type Factor IX, and wherein the Factor IX variant polypeptide comprises an amino acid sequence having at least 90% sequence identity to SEQ ID NO: 1.

Another exemplary embodiment is a Factor IX variant polypeptide comprising the amino acid H at a position corresponding to position 410 of wild-type Factor IX and an amino acid selected from the group consisting of V, T and W (e.g. V or T, particularly V) at a position corresponding to position 338 of wild-type Factor IX, and wherein the Factor IX variant polypeptide comprises an amino acid sequence having at least 95% sequence identity to SEQ ID NO: 1.

As noted above, in any of these embodiments the Factor IX variant polypeptide is biologically active, i.e. it is capable of activating Factor X (i.e. generating Factor Xa).

The Factor IX variant polypeptides of the invention are typically comprised of naturally occurring amino acid. However, one or more non-naturally occurring amino acids can also be present.

A percentage sequence identity between two amino acid sequences means that, when aligned, that percentage of amino acids is the same in comparing the two sequences. The percentage sequence identity is calculated as the percentage of identical amino acids within the aligned sequences, excluding the amino acids in positions 338 and/or 410. A sequence that "has" (or "having") x % sequence identity to another sequence means that the sequence is x % identical to that other sequence.

For example, in embodiments where the amino acid in the Factor IX variant polypeptide that corresponds to position 410 of SEQ ID NO: 1 is different from the amino acid in that position in SEQ ID NO: 1, but the amino acid in the Factor IX variant polypeptide that corresponds to position 338 of SEQ ID NO: 1 is the same as the amino acid in that position in SEQ ID NO: 1, then the percentage sequence identity is calculated as the percentage of identical amino acids within the aligned regions, and excluding the amino acid in position 410. However, in embodiments where the amino acid in the Factor IX variant polypeptide that corresponds to position 410 of SEQ ID NO: 1 is different from the amino acid in that position in SEQ ID NO: 1, and the amino acid in the Factor IX variant polypeptide that corresponds to position 338 of SEQ ID NO: 1 is different from the amino acid in that position in SEQ ID NO: 1, then the percentage sequence identity is calculated as the percentage of identical amino acids within the aligned regions, and excluding the amino acids in positions 410 and 338.

In embodiments in which the Factor IX variant polypeptide is linked with a half-life enhancing portion (e.g. albumin), optionally via a cleavable linker (i.e. a fusion protein), or is linked with some other polypeptide when determining the sequence identity with SEQ ID NO: 1 only the Factor IX variant polypeptide portion of the molecule is considered for the purposes of calculating the sequence identity, i.e. excluding any linker and excluding the half-life enhancing portion of the molecule. This applies also when e.g. the linker is derived from a Factor IX sequence.

Similarly, where the Factor IX variant polypeptide corresponds to one or more fragments of the full-length Factor IX polypeptide (e.g. it is an activated form of Factor IX), when determining the sequence identity with SEQ ID NO: 1 any portions that are present in SEQ ID NO: 1 but missing in the Factor IX variant polypeptide (e.g. the activation peptide) are excluded for the purposes of calculating the sequence identity.

In a particular embodiment, all residues in the Factor IX variant polypeptide other than at positions 338 and 410 are wild-type, i.e. there is a 100% sequence identity with SEQ ID NO: 1 excluding the amino acids in positions 338 and 410.

In some embodiments, the Factor IX variant polypeptide is as defined in SEQ ID NOs: 11, 12, 13 or 14, for example SEQ ID NOs: 11, 12 or 13, in particular SEQ ID NOs: 11 or 12. SEQ ID NO: 11 defines a Factor IX variant polypeptide having a particularly high Factor IX specific activity. The Factor IX variant polypeptide may also be a biologically active fragment (i.e. it has procoagulant activity, for example activated Factor IX) of any one of SEQ ID NOs: 11, 12, 13 or 14, such as SEQ ID NOs: 11, 12 or 13, and encompassing amino acids 338 and 410 as defined in any one of SEQ ID NOs: 11, 12, 13 or 14, such as SEQ ID NOs: 11, 12 or 13. The Factor IX variant may also be a polypeptide having at least 75%, at least 80%, at least 85%, at least 90%, at least 95%, or at least 98% or at least 99% sequence identity to SEQ ID NOs: 11, 12, 13 or 14, such as SEQ ID NOs: 11, 12 or 13, or to a fragment of those SEQ ID NOs. In any of these embodiments the Factor IX variant polypeptide is biologically active, i.e. it is capable of activating Factor X (i.e. generating Factor Xa).

The Factor IX variant as described herein may be part of a molecule comprising the variant, and further comprising one or more additional portions. For example, the Factor IX variant polypeptide may be linked to a half-life enhancing portion. The half-life enhancing portion may be another different polypeptide such as albumin (e.g. recombinant human albumin), the Fc portion of an antibody (e.g. IgG Fc), a C-terminal peptide of human chorionic gonadotropin (CTP), or an unstructured recombinant polypeptide (e.g. XTEN). The Factor IX variant may also be pegylated. The Factor IX variant may be linked in any of these ways directly or via a linker. The linker may be a cleavable linker, for example a proteolytically cleavable linker. Alternatively, a non-cleavable linker may be used.

Alternatively, the molecule of the invention may consist of the Factor IX variant polypeptide provided herein, i.e., without any additional portion(s), such as half-life enhancing portion(s). The invention also provides a nucleic acid encoding a Factor IX variant of the invention, or encoding a molecule comprising the same, for example for use in gene therapy, e.g. in the prevention or treatment of hemophilia B.

The invention also provides a vector comprising the nucleic acid. Suitable exemplary vectors are known to the person skilled in the art and can be selected from the group consisting of an adenoviral vector, an adenovirus-associated vector, a retroviral vector, a plasmid, and a lentiviral vector.

Another aspect of the invention includes a cell comprising the nucleic acid or vector of the invention.

Further provided is a pharmaceutical composition comprising the Factor IX variant, nucleic acid, vector, or the cell as described herein, and a pharmaceutically acceptable carrier.

The Factor IX variant, nucleic acid, vector or cell may be provided in purified form. The Factor IX variant, nucleic acid, vector or cell may be provided in isolated form. The Factor IX variant polypeptide may be post-translationally modified.

The invention also provides the Factor IX variant, molecule comprising the same, nucleic acid, vector, cell or pharmaceutical composition as described herein for use as a medicament.

For example, the invention provides a method for the treatment or prophylaxis of a blood coagulation disorder in a subject in a patient in need thereof comprising administering a therapeutically effective amount of the Factor IX variant (or a molecule comprising the Factor IX variant, a nucleic acid molecule encoding the Factor IX variant, etc.) to the subject. Such methods have efficacy in the prophylaxis or treatment of disorders where a pro-coagulant activity is needed (e.g., to prevent, reduce or inhibit bleeding) and include, without limitation, hemophilia, particularly hemophilia B. The invention therefore provides a method for the treatment or prophylaxis of a blood coagulation disorder in a subject, in particular the treatment or prophylaxis of bleeding in patients with hemophilia B (congenital factor IX deficiency).

The invention also provides the Factor IX variant (or a molecule comprising the Factor IX variant, a nucleic acid molecule encoding the Factor IX variant, etc.) for use in the treatment or prophylaxis of a blood coagulation disorder in a subject, in particular the treatment or prophylaxis of bleeding in patients with hemophilia B.

Also provided is the use of the Factor IX variant (or a molecule comprising the Factor IX variant, a nucleic acid molecule encoding the Factor IX variant, etc.) for the manufacture of a medicament for the treatment or prophylaxis of a blood coagulation disorder in a subject, in particular the treatment or prophylaxis of bleeding in patients with hemophilia B.

The treatment or prophylaxis may include on-demand control of bleeding episodes, perioperative management of bleeding, and/or routine prophylaxis to prevent or reduce the frequency of bleeding episodes. For example, treatment may include on-demand control of bleeding episodes or perioperative management of bleeding. Prophylaxis may include prevention of bleeding episodes or reducing the frequency of bleeding episodes.

The subject is typically a human. The subject may be an adult or a child. The subject may have a basal (without prophylaxis or treatment) plasma Factor IX activity of 5% or less, 4% or less, 3% or less, 2% or less, between 1-5%, or 1% or less, compared to the plasma Factor IX activity of a healthy subject.

The treatment or prevention may involve gene therapy, such as human gene therapy. The gene therapy is typically administered as a vector, such as an adenovirus-associated vector, encoding the Factor IX variant or encoding a molecule comprising the Factor IX variant of the invention.

Also provided is a method of producing a Factor IX variant or a molecule comprising a Factor IX variant of the invention, comprising culturing cells under conditions such that the molecule is expressed.

Factor IX Variant Polypeptide

A Factor IX variant polypeptide according to the invention is derived from a polypeptide sequence of wild-type Factor IX. The variant differs at one or more amino acid positions from the corresponding positions in the wild-type Factor IX, i.e. the variant has one or more amino acid substitutions relative to the corresponding positions in the wild-type Factor IX.

For example, a Factor IX variant polypeptide according to the invention may comprise the amino acid H at a position corresponding to position 410 of wild-type Factor IX, and an amino acid other than R at a position corresponding to position 338 of wild-type Factor IX. A Factor IX variant polypeptide according to the invention may additionally comprise amino acid substitutions at other positions relative to wild-type Factor IX.

The variant has the biological function of a Factor IX, i.e. the variant is able to generate Factor Xa, optionally after the Factor IX variant polypeptide has been converted to its active form (Factor IXa) by excision of the activation peptide. Activation cleavage of Factor IX can be achieved in vitro e.g. by Factor XIa or Factor VIIa/TF. Suitable in vitro assays to measure Factor IX activity are known to the person skilled in the art (e.g. one-stage clotting assay such as an aPTT assay, chromogenic assay, etc.). An in vitro aPTT-based one stage clotting assay is a preferred assay for determining Factor IX activity, typically as described in Example 3.

The variant typically has an increased Factor IX specific activity compared to a wild-type Factor IX polypeptide from which the variant is derived, as a result of at least one 'gain of function' amino acid substitution relative to the wild-type, i.e. the variant is 'hyperactive'.

The Factor IX variant polypeptide can be derived from a Factor IX polypeptide sequence of any mammalian species. In a particular embodiment, the Factor IX variant polypeptide is derived from a Factor IX polypeptide sequence of human origin. Gene ID: 2158 (https://www.ncbi.nlm.nih-.gov/gene/2158), GenBank Accession Nos. NM_000133.3 (https://www.ncbi.nlm.nih.gov/nuccore/NM_000133.3), NP_000124.1 (https://www.ncbi.nlm.nih.gov/protein/NP_000124.1?report=gemept), and UniProt entry P00740 (https://www.uniprot.orq/uniprot/P00740) provide examples of the amino acid and/or nucleotide sequences of wild-type human Factor IX.

The Factor IX variant polypeptide according to the invention may be derived from mature (i.e. excluding signal peptide and propeptide) wild-type Factor IX, for example of human origin, the amino acid sequence of which is shown in SEQ ID NO: 1. That polypeptide sequence is 'isoform 1' of human Factor IX.

The polypeptide of SEQ ID NO: 1 has the amino acid R at position 338 and the amino acid E at position 410 (references to amino acids herein use the single-letter codes as widely known in the art; for example, "R" stands for arginine, and "E" stands for glutamic acid, etc.). Positions 338 and 410 in SEQ ID NO: 1 are in the Peptidase 51 domain. Positions 338 and 410 are indicated in bold and underline below. The 35-aa activation peptide which is excised to form FIXa (activated Factor IX) is underlined.

(SEQ ID NO: 1)

YNSGKLEEFVQGNLERECMEEKCSFEEAREVFENTERTTEFWKQYVDGDQ

CESNPCLNGGSCKDDINSYECWCPFGFEGKNCELDVTCNIKNGRCEQFCK

NSADNKVVCSCTEGYRLAENQKSCEPAVPFPCGRVSVSQTSKLTRAETVF

PDVDYVNSTEAETILDNITQSTQSFNDFTRVVGGEDAKPGQFPWQVVLNG

-continued

```
KVDAFCGGSIVNEKWIVTAAHCVETGVKITVVAGEHNIEETEHTEQKRNV

IRIIPHHNYNAAINKYNHDIALLELDEPLVLNSYVTPICIADKEYTNIFL

KFGSGYVSGWGRVFHKGRSALVLQYLRVPLVDRATCLRSTKFTIYNNMFC

AGFHEGGRDSCQGDSGGPHVTEVEGTSFLTGIISWGEECAMKGKYGIYTK

VSRYVNWIKEKTKLT
```

An exemplary polynucleotide coding sequence for the polypeptide of SEQ ID NO: 1 is shown in SEQ ID NO: 2.

The term "derived from a polypeptide sequence of wild-type Factor IX" (or similar wording) means that the Factor IX variant polypeptide has some degree of sequence identity with wild-type Factor IX polypeptide when the two sequences are aligned. For example, the Factor IX variant polypeptide may have at least 70% etc. sequence identity to SEQ ID NO: 1, as described above. The Factor IX variant polypeptide is biologically active, i.e. it is capable of activating Factor X (i.e. generating Factor Xa).

The term "wild-type Factor IX" refers to a Factor IX polypeptide sequence that occurs naturally, i.e. the sequence has not been artificially modified relative to the sequence of the naturally occurring polypeptide sequence. This means that none of the amino acids in the naturally occurring polypeptide sequence has been substituted with a different amino acid. SEQ ID NO: 1 is an example of a wild-type polypeptide sequence, but fragments, truncations, etc. are also encompassed by the term, as exemplified below. For example, the term includes polypeptides with a modified N-terminal or C-terminal end including terminal amino acid deletions or additions, as long as those polypeptides substantially retain the activity of Factor IX. The term also includes any natural polymorphic variants of Factor IX. For example, a common natural polymorphic variant which occurs with a frequency of 33% is a Factor IX polypeptide presenting an alanine (A) in a position corresponding to position T148 in SEQ ID NO: 1. This T148A polymorphic variant is shown in SEQ ID NO: 7. All references to SEQ ID NO: 1 herein may therefore also refer to SEQ ID NO: 7.

The Factor IX variant polypeptide may also be derived from a wild-type Factor IX that includes the signal and/or the propeptide, as shown in SEQ ID NO: 3. SEQ ID NO: 3 includes both the signal peptide (aa 1-28) and the propeptide (aa 29-46). It is known in the art as the precursor of human Factor IX, or as the prepropeptide Factor IX. Factor IX with propeptide but lacking the signal peptide is also known as a propeptide Factor IX. An exemplary polynucleotide coding sequence encoding the polypeptide of SEQ ID NO: 3 is shown in SEQ ID NO: 4.

The Factor IX variant polypeptide may also be derived from one or more fragments of wild-type Factor IX, for example it may be derived from activated Factor IX which contains two fragments of Factor IX (it is missing the intervening 'activation peptide' that is present in SEQ ID NO: 1). SEQ ID NOs 5 and 6 show the light chain and heavy chain, respectively, of human activated Factor IX, which are held together by a disulphide bridge. Another example is isoform 2 of human Factor IX, which lacks the 38-aa stretch at positions 47-84 of SEQ ID NO: 1.

Alternatively, the Factor IX variant polypeptide may be derived from a truncation or a fusion of wild-type Factor IX.

The Factor IX variant polypeptide therefore may take various different forms, as long as it maintains the biological function of Factor IX as described above (i.e. it is a functional Factor IX variant polypeptide). Accordingly, the Factor IX variant polypeptide of the invention may be a variant of a wild-type prepropeptide Factor IX, propeptide Factor IX, mature Factor IX, activated Factor IX, or their fragments, truncations, fusions, isoforms, polymorphic variants, etc. All of these forms of Factor IX are collectively referred to herein, unless indicated otherwise, as 'Factor IX'.

References to amino acid positions made herein are relative to the numbering in SEQ ID NO: 1, i.e. the amino acid positions are those corresponding to that position in SEQ ID NO: 1. This means that, for example, if a Factor IX variant polypeptide is based on SEQ ID NO: 1 but additionally includes the propeptide and signal peptide of Factor IX (which together are 46 amino acids long, and are missing from SEQ ID NO: 1), then e.g. "a Factor IX variant polypeptide comprising the amino acid H at a position corresponding to position 410 of wild-type Factor IX" means that the Factor IX variant polypeptide comprises H at position 456 of the variant polypeptide (410+46). Similarly, if the Factor IX variant polypeptide is based on an activated version of Factor IX (which lacks the 35-aa activation peptide of SEQ ID NO: 1), then e.g. "a Factor IX variant polypeptide comprising the amino acid H at a position corresponding to position 410 of wild-type Factor IX" means that the Factor IX variant polypeptide comprises H at position 375 of the variant polypeptide (410-35), which corresponds to position 230 of the heavy chain of activated Factor IX. The skilled person is able to determine the relevant positions in a Factor IX variant polypeptide by comparing the polypeptide sequence of the variant with the polypeptide sequence of SEQ ID NO: 1 and identifying the aligning portion(s).

The Factor IX variant polypeptide (or a molecule comprising the same) may be provided as an "isolated" or as a "purified" polypeptide. This term may refer to a polypeptide produced by expression of an isolated nucleic acid molecule of the invention. Alternatively, this term may refer to a protein which has been sufficiently separated from other proteins with which it would naturally be associated (e.g., so as to exist in "substantially pure" form). "Isolated" is not meant to exclude artificial or synthetic mixtures with other compounds or materials, or the presence of impurities that do not interfere with the fundamental activity, and that may be present, for example, due to incomplete purification, or the addition of stabilizers.

The term "substantially pure" refers to a preparation comprising at least 50-60% by weight the compound of interest (e.g., the Factor IX variant polypeptide or a molecule comprising the same), particularly at least 75% by weight, or at least 90-99% or more by weight of the compound of interest. Purity may be measured by methods appropriate for the compound of interest (e.g. chromatographic methods, agarose or polyacrylamide gel electrophoresis, HPLC analysis, and the like).

In some embodiments of this invention the Factor IX variant is provided as a nucleic acid, for example for use in gene therapy, as described in more detail below. In such embodiments, a nucleic acid encoding a Factor IX variant polypeptide as described herein is provided. The nucleic acid may be administered with a viral vector, e.g. an adenovirus-associated vector, or a lentivirus vector, to the subject. Gene editing approaches may also be used to provide a subject with a Factor IX variant polypeptide as described herein.

A Factor IX variant polypeptide (or a molecule comprising the same, or a nucleic acid encoding the same, or a pharmaceutical composition comprising the same) according to the invention may be therapeutic, i.e. when administered to a subject (e.g. a human) with Factor IX deficiency such as hemophilia B, a prophylactic or therapeutic effect can be observed. This means that the plasma levels of Factor IX activity can be increased, at least temporarily. Such a prophylactic or therapeutic effect can be determined for example by measuring the plasma Factor IX activity in the subject after prophylaxis or treatment, and comparing it to the plasma Factor IX activity in that subject before prophylaxis or treatment. An increase in Factor IX activity after prophylaxis or treatment indicates a prophylactic or therapeutic effect. A prophylactic or therapeutic effect is also achieved where the Factor IX activity after prophylaxis or treatment is sufficient to prevent, reduce or inhibit bleeding. The Factor IX activity after prophylaxis or treatment may be outside of the pathological range. The Factor IX activity after prophylaxis or treatment may be comparable to the Factor IX activity in normal human plasma. Factor IX activity can be measured using any Factor IX activity assay known to the skilled person, for example using an aPTT assay (a decrease in aPTT value indicates increased Factor IX activity). In a preferred embodiment therefore Factor IX activity is determined using an in vitro aPTT-based one stage clotting assay, typically as described in Example 3.

A Factor IX variant polypeptide (or a molecule comprising the same) according to the invention is preferably non-immunogenic in a subject, typically a human subject. This means that after administration of the polypeptide or molecule comprising the same to the subject, or after in vivo expression of the polypeptide or molecule in the subject, the subject does not exhibit a measurable immune response (e.g. neutralising antibodies) against the variant polypeptide or molecule beyond that observed against the corresponding wild-type polypeptide. However, any such immune response can be avoided or treated if necessary, e.g. with corticosteroids. Tests for evaluating immunogenicity are known in the art, e.g. Example 11 of reference 1.

Preparing a Factor IX Variant Polypeptide

A Factor IX variant polypeptide of the invention (or a molecule comprising the same) can be made using standard techniques well known to the skilled person in the art, such as described in Example 1.

For example, the cDNA sequence of a wild-type Factor IX (e.g. SEQ ID NO: 2) may be modified using standard mutagenesis techniques (e.g. site-directed mutagenesis) so that it encodes the desired Factor IX variant polypeptide, e.g. encoding the amino acid H at a position corresponding to position 410 of wild-type Factor IX (which encodes the amino acid E at that position) and encoding the amino acid V at a position corresponding to position 338 of wild-type Factor IX (which encodes the amino acid R at that position). An N-terminal leader peptide for the purposes of recombinant protein production can be used, based on the natural Factor IX leader peptide (as shown in SEQ ID NO: 3) or alternatives known to the skilled person in the art.

The cDNA sequence may be inserted into a suitable expression plasmid to express the recombinant Factor IX variant polypeptide. This is typically performed using mammalian cells (e.g. HEK for transient expression or a CHO cell line for stable expression), although other types of cells that can produce glycosylated and correctly folded proteins can also be used. The recombinant Factor IX variant polypeptide may subsequently be purified, for example using anion exchange chromatography.

The recombinant Factor IX variant polypeptide may be combined with other agents and/or with a pharmaceutically acceptable carrier. The recombinant Factor IX variant polypeptide may also be lyophilised.

A Molecule Comprising a Factor IX Variant Polypeptide

The Factor IX variant polypeptide of the invention may be provided on its own, i.e. without any non-Factor IX portions linked to the Factor IX variant polypeptide. In such embodiments "a molecule comprising a Factor IX variant polypeptide" refers to a molecule that consists of the Factor IX variant polypeptide.

Alternatively, the Factor IX variant polypeptide of the invention may be provided as part of a molecule comprising the variant, and further comprising one or more additional portions. The one or more additional portions are typically different from Factor IX, i.e. they do not have the biological function of Factor IX as defined above (they do not have the ability to generate Factor Xa). This means that fragments of Factor IX, e.g. linkers comprising a fragment of a Factor IX-derived polypeptide sequence, but which do not on their own have the function of Factor IX, may be such "one or more additional portions", i.e. they are not part of the Factor IX variant polypeptide but they may be part of the molecule that comprises the Factor IX variant polypeptide.

Half-Life Enhancing Portion and Linker

An exemplary molecule comprising a Factor IX variant polypeptide is a molecule wherein the Factor IX variant polypeptide is linked to a half-life enhancing portion.

The half-life enhancing portion may comprise one or more polypeptides (half-life enhancing polypeptides, HLEPs), for example albumin or an immunoglobulin, or a fragment or derivative of either. In one embodiment, the HLEP is albumin, e.g. recombinant human albumin. In another embodiment, the HLEP is a fragment of an antibody (immunoglobulin), such as the Fc fragment, e.g. IgG Fc, such as IgG1 Fc. Alternatively, the HLEP may be a C-terminal peptide of human chorionic gonadotropin (CTP). The HLEP may also be an unstructured recombinant polypeptide (e.g. XTEN). Such molecules are also referred to in the art as fusion polypeptides.

The Factor IX variant may be linked to the HLEP via a cleavable linker. Typically the cleavable linker is cleavable by the same protease that activates Factor IX. Such cleavable linkers therefore provide a high molar specific activity of the fusion polypeptide. Suitable cleavable linkers are taught, for example, in reference 1.

The Factor IX variant may also be PEGgylated.

A molecule comprising a Factor IX variant polypeptide of the invention may comprise one half-life enhancing portion, or more than one half-life enhancing portions. The wording "a half-life enhancing portion" therefore covers one or more half-life enhancing portions. The half-life enhancing portions may be of the same type. The half-life enhancing portions may be of different types. For example, the Factor IX variant polypeptide may be linked to XTEN (e.g. XTEN72) and additionally to an Fc domain (e.g. human IgG1 Fc).

Preferably, the half-life enhancing portion is capable of extending the half-life of the Factor IX variant polypeptide in vivo (in plasma) by at least about 25% as compared to the non-fused Factor IX variant polypeptide. Preferably, the half-life enhancing portion is capable of extending the half-life of the Factor IX variant polypeptide in vivo (in plasma) by at least about 50%, and more preferably by more than 100%.

The in vivo half-life of the fusion polypeptides of the invention is generally determined as the terminal half-life or the $\beta$-half-life.

Albumin

As used herein, "albumin" refers collectively to an albumin polypeptide or amino acid sequence, or an albumin fragment, variant or analog having one or more functional activities (biological activities) of albumin. In particular, "albumin" may refer to human albumin (HA) or a fragment thereof, especially the mature form of human albumin as shown in SEQ ID NO: 9 herein. The albumin may also be derived from other species, in particular other vertebrates.

The albumin portion of the fusion polypeptide may comprise the full length of the HA sequence as described in SEQ ID NO: 9, or it may include one or more fragments thereof that are capable of stabilizing or prolonging the therapeutic activity of the Factor IX variant polypeptide. Such fragments may be of 10 or more amino acids in length or may include about 15, 20, 25, 30, 50, or more contiguous amino acids from the HA sequence or may include part or all of the specific domains of HA. These and other suitable albumin portions (including variants) are described in reference 1.

Structurally related family members of the albumin family may also be used as HLEPs. For example, alpha-fetopolypeptide (AFP, reference 2) is a member of the albumin family and may also be used to enhance the half-life of a Factor IX variant polypeptide. Such half-life enhancing polypeptides are described in reference 3. Another option is afamin (AFM, reference 4) or vitamin D binding polypeptide (DBP, reference 5). Fragments of these polypeptides may also be used.

In embodiments that use albumin HLEPs, the albumin is typically provided as a genetic fusion with the Factor IX variant polypeptide. This means that a single cDNA molecule encodes the Factor IX variant polypeptide and the albumin portion, optionally with an intervening sequence encoding a linker, such as a cleavable linker.

An exemplary Factor IX variant polypeptide (R338V+E410H) albumin fusion polypeptide with an intervening cleavable linker is shown in SEQ ID NO: 15.

Immunoglobulin

An immunoglobulin (Ig) or a fragment thereof may also be used as a HLEP. An example of a suitable immunoglobulin is IgG, or an IgG-fragment, such as an Fc region. The Fc region may be an Fc domain (e.g., two polypeptide chains each of which comprises the hinge region (or part of the hinge region), the CH2 region and the CH3 region). Thus in a particular embodiment a Factor IX variant polypeptide of the invention is fused to an Fc domain, directly or via a linker. In embodiments that use a linker, the linker may be cleavable.

Monomers, dimers and hybrids are all encompassed. For example, the invention provides a heterodimer comprising two polypeptide chains, wherein the first chain comprises a Factor IX variant polypeptide of the invention linked to the hinge region (or part of the hinge region), the CH2 region and the CH3 region of an immunoglobulin (e.g. IgG1), and the second chain comprises the hinge region (or part of the hinge region), the CH2 region and the CH3 region of an immunoglobulin (e.g. IgG1).

In another embodiment the invention provides a homodimer comprising two polypeptide chains, wherein each chain comprises a Factor IX variant polypeptide of the invention linked to the hinge region (or part of the hinge region), the CH2 region and the CH3 region of an immunoglobulin (e.g. IgG1).

The invention also provides a monomer comprising a Factor IX variant polypeptide of the invention linked to the hinge region (or part of the hinge region), the CH2 region and the CH3 region of an immunoglobulin (e.g. IgG1).

Other examples of suitable Factor IX IgG Fc fusion molecule configurations are found, e.g., in reference 6.

An exemplary Fc polypeptide (derived from the human IgG1 Fc domain) for use with a Factor IX variant polypeptide of the invention is shown in SEQ ID NO: 16. Another exemplary Fc polypeptide (derived from the human IgG1 Fc domain) for use with a Factor IX variant polypeptide of the invention is shown in SEQ ID NO: 17.

In any of these embodiments, the Factor IX variant polypeptide may be linked directly or via a linker to the Fc region. In embodiments that use a linker, the linker may be cleavable or non-cleavable. In particular embodiments, the linker is cleavable. An exemplary cleavable linker is shown in SEQ ID NO: 8.

In a specific embodiment, the invention provides a molecule comprising a Factor IX variant polypeptide as described herein linked to a human IgG1 Fc region (e.g. SEQ ID NO: 16 or SEQ ID NO: 17). The human IgG1 Fc region may be linked to the Factor IX variant polypeptide directly or via a linker, optionally a cleavable linker.

In another specific embodiment, the invention provides a heterodimer comprising two polypeptide chains, wherein the first chain comprises a Factor IX variant polypeptide of the invention linked to a human IgG1 Fc region, and wherein the second polypeptide chain comprises a human IgG1 Fc region. The human IgG1 Fc region may be SEQ ID NO: 16 or SEQ ID NO: 17. In the first polypeptide chain, the human IgG1 Fc region may be linked to the Factor IX variant polypeptide directly or via a linker, optionally a cleavable linker.

Eftrenonacog alfa (Alprolix®) is an example of a Factor IX Fc fusion. See also references 7, 8 or 9.

C-Terminal Peptide of Human Chorionic Gonadotropin (CTP)

Another exemplary half-life enhancing portion for use with a Factor IX variant polypeptide of the invention is a C-terminal peptide of human chorionic gonadotropin (CTP). CTP is based on a natural peptide of 31 amino acids length, the C-terminal peptide of the beta chain of human chorionic gonadotropin (hCG).

One or more units of CTP can be fused to a Factor IX variant polypeptide of the invention. The one or more units of CTP can be fused to the N-terminus and/or to the C-terminus of Factor IX, preferably to the C-terminus.

In one embodiment, this invention provides a CTP-modified Factor IX variant polypeptide comprising a Factor IX variant polypeptide as described herein linked with three to five CTPs, optionally wherein the CTPs are attached to the C-terminus of the Factor IX variant polypeptide. In a specific embodiment, three tandem units of CTP are attached the Factor IX variant polypeptide, optionally at the C-terminus of the Factor IX variant polypeptide.

In any of these embodiments, at least one of the CTP may be attached to the Factor IX variant polypeptide via a linker. The linker may be a peptide bond. The linker may be cleavable.

In an exemplary embodiment, the CTP sequence comprises SEQ ID NO: 18. In another exemplary embodiment, the CTP sequence comprises SEQ ID NO: 19. In another exemplary embodiment, the CTP sequence comprises SEQ ID NO: 20.

Other suitable CTP sequences and related methods are known to the skilled person in the art, e.g. see references 10, 11 or 12.

Unstructured Recombinant Polypeptide

Another exemplary half-life enhancing portion for use with a Factor IX variant polypeptide of the invention is an unstructured recombinant polypeptide. An example of such an unstructured recombinant polypeptide is XTEN, see e.g. reference 13.

In one embodiment, this invention therefore provides a Factor IX variant polypeptide fused with at least one XTEN. XTEN may be fused to the Factor IX variant polypeptide by insertion into the Factor IX variant polypeptide sequence while maintaining the biological activity of Factor IX. For example, the XTEN may be inserted between two neighbouring amino acids in the activation peptide of the Factor IX variant at a position that does not prevent cleavage of the activation peptide during coagulation when XTEN is inserted. Alternatively, XTEN may fused to the C-terminus and/or N-terminus of the Factor IX variant polypeptide, preferably the C-terminus. XTEN may be fused to the C-terminus and/or N-terminus (preferably C-terminus) of the Factor IX variant polypeptide via a linker, e.g. a cleavable linker. The linker may be cleavable by thrombin.

A preferred XTEN is XTEN72. An exemplary XTEN72 sequence is shown in SEQ ID NO: 21. An alternative XTEN sequence is shown in SEQ ID NO: 22. Other suitable sequences and methods are disclosed in e.g. references 14, 15 or 16.

In a specific embodiment, the invention provides a Factor IX variant polypeptide which comprises XTEN72 linked to the activation peptide and wherein the Factor IX variant polypeptide is also linked to a human IgG1 Fc domain at the C-terminus of the Factor IX variant polypeptide.

PEGylation

Another exemplary half-life enhancing portion for use with a Factor IX variant polypeptide of the invention is polyethylene glycol (PEG).

Glycopegylation is within the scope of the term "PEGylation" as used herein. For example, a ca. 40 kDa PEG portion may be covalently attached to the Factor IX variant polypeptide, for example via a specific N-linked glycan within the activation peptide. An example of a glycopegylated Factor IX polypeptide is nonacog beta pegol (Refixia®) (see also reference 17), in which an average of one non-reducing end of a glycan at N157 or N167 of Factor IX (numbering according to SEQ ID NO: 1) is attached to neuraminic acid conjugated to two PEG polymers (total average molecular weight of the polymers is ca. 42 kDa) via the amino group. PEGylation of Factor IX polypeptide is also taught, for example, in references 18, 19 and 20.

Linker

Molecules of the invention comprising a half-life enhancing portion may employ a cleavable linker, in particular a proteolytically cleavable linker. The linker is generally positioned between the Factor IX variant polypeptide and a half-life enhancing portion. The linker may liberate the Factor IX variant polypeptide upon cleavage of the linker by a protease of the coagulation cascade, e.g. a protease that is also capable of converting the Factor IX variant polypeptide to its activated form, e.g., FXIa or VIIa/tissue factor (TF). Cleavable linkers are particularly useful when the HLEP is albumin.

Although it is desirable to have an enhanced Factor IX in vivo half-life, it is desirable to limit the half-life of the Factor IX once it has been activated, to reduce the risk of a prothrombotic effect, especially with a hyperactive Factor IX variant polypeptide. In some embodiments therefore, a cleavable linker links the Factor IX variant polypeptide to a half-life enhancing portion, thereby providing a Factor IX variant polypeptide with a longer half-life relative to a non-fusion polypeptide. However, once bleeding occurs and the coagulation cascade has been initiated, a protease of the coagulation cascade activates the Factor IX variant polypeptide which has increased specific activity relative to e.g. the corresponding wild-type Factor IX. At the same time, the linker is cleaved and the activated Factor IX variant polypeptide is liberated from the half-life enhancing portion, thereby reducing the risk of a prothrombotic effect due to any prolonged increased Factor IX activity.

The linker may be a fragment of Factor IX, preferably a fragment that is involved in Factor IX activation. For example, the linker may comprise such a fragment of a Factor IX sequence, extended by an N-terminal residue, such as a proline residue. An exemplary cleavable linker is shown in SEQ ID NO: 8. Other cleavable linkers are described in reference 1.

A molecule of the invention comprising a Factor IX variant polypeptide linked to a half-life enhancing portion via an intervening cleavable linker may have at least 25% higher molar specific activity compared to the corresponding molecule with a non-cleavable linker (e.g. GGGGGGV), when measured in at least one coagulation-related assay, examples of which are known to the skilled person in the art, e.g. an aPTT one-stage assay, for example as described in Example 3. Preferably, a molecule of the invention comprising a Factor IX variant polypeptide linked to a half-life enhancing portion via an intervening cleavable linker has at least 50%, more preferably at least 100% increased molar specific activity compared to the corresponding molecule without cleavable linker.

Factor IX Activity

Factor IX activity may be determined using any suitable assay. Factor IX activity is generally referred to in the art as the specific activity (also referred to herein as molar specific activity). The molar specific activity is defined as the activity per mole (or e.g. nmole) of the polypeptide of interest. Calculation of the molar specific activity allows a direct comparison of the activity of different polypeptides. The molar specific activity is not affected by the different molecular weights or optical densities of the different polypeptides. The molar specific activity may be calculated as exemplified in table 2 of reference 1.

Various Factor IX activity assays are well known to the skilled person in the art, e.g. one-stage assay, e.g. aPTT assay, and chromogenic assay.

For example, an activated partial thromboplastin time (aPTT) assay is a well-known Factor IX assay. In a preferred embodiment therefore Factor IX activity is determined using an in vitro aPTT-based one stage clotting assay. Such an exemplary assay is described in Example 3 below. It is commercially available (e.g., Pathromtin® SL, Siemens Healthcare). Incubation of test plasma (e.g. Factor IX depleted plasma containing an amount of sample, e.g. from a subject, a cell culture supernatant, or a purified Factor IX polypeptide) with the optimal quantity of phospholipids and a surface activator leads to activation of factors of the intrinsic coagulation system. The addition of calcium ions triggers the coagulation process; the time to formation of a fibrin clot is measured. An internal substandard calibrated against the WHO International FIX concentrate Standard can be used as a reference.

However, other known Factor IX activity assays may also be used to determine the specific activity of a Factor IX polypeptide.

An "increase" in specific activity relative to control occurs when such an increase is observed in at least one Factor IX activity assay, e.g. a reduction in aPTT value when Factor IX activity is measured using an in vitro aPTT-based one stage clotting assay, for example as described in Example 3.

Nucleic Acids

The invention also provides a nucleic acid encoding a Factor IX variant of the invention or encoding a molecule comprising the same, for example for use in gene therapy, e.g. in the prevention or treatment of hemophilia B.

The nucleic acid may be a DNA (e.g. cDNA). The nucleic acid may be an RNA (e.g. mRNA). The nucleic acid may be provided as an isolated nucleic acid. This term, when applied to DNA, refers to a DNA molecule that is separated from sequences with which it is immediately contiguous (in the 5' and 3' directions) in the naturally occurring genome of the organism from which it originates. For example, the "isolated nucleic acid" may comprise a DNA or cDNA molecule inserted into a vector, such as a plasmid or virus vector, or integrated into the DNA of a prokaryote or eukaryote. With respect to RNA molecules of the invention, the term "isolated nucleic acid" primarily refers to an RNA molecule encoded by an isolated DNA molecule as defined above. Alternatively, the term may refer to an RNA molecule that has been sufficiently separated from RNA molecules with which it would be associated in its natural state (i.e., in cells or tissues), such that it exists in a "substantially pure" form.

Vectors

The invention also provides a vector comprising the nucleic acid. Suitable exemplary vectors are known to the person skilled in the art and can be selected from the group consisting of an adenoviral vector, an adenovirus-associated vector, a retroviral vector, a plasmid, and a lentiviral vector.

The term "vector" refers to a carrier nucleic acid molecule (e.g., RNA or DNA) into which a nucleic acid sequence can be inserted, e.g., for introduction into a host cell where it may be expressed and/or replicated. The term includes a plasmid. An "expression vector" is a specialized vector that contains a gene or nucleic acid sequence with the necessary regulatory regions needed for expression in a host cell.

The term "operably linked" means that the regulatory sequences necessary for expression of a coding sequence are placed in the DNA molecule in the appropriate positions relative to the coding sequence so as to effect expression of the coding sequence. This same definition is sometimes applied to the arrangement of coding sequences and transcription control elements (e.g. promoters, enhancers, and termination elements) in an expression vector. This definition is also sometimes applied to the arrangement of nucleic acid sequences of a first and a second nucleic acid molecule wherein a hybrid nucleic acid molecule is generated.

In a particular embodiment of the invention, the vector is a viral vector. Viral vectors, with or without tissue specific promoters/enhancers, which may be used with the present invention include, but are not limited to: adeno-associated virus (AAV) vectors (e.g., AAV1, AAV2, AAV3, AAV4, AAV5, AAV6, AAV7, AAV8, AAV9, AAV10, AAV11, AAV12, AAVrh10, or other derivatives and/or alternate serotypes) and hybrid AAV vectors (e.g., a combinatorial hybrid of 2, 3, 4, 5, or more serotypes), lentivirus vectors and pseudo-typed lentivirus vectors (e.g., Ebola virus, vesicular stomatitis virus (VSV), and feline immunodeficiency virus (FIV)), herpes simplex virus vectors, vaccinia virus vectors, and retroviral vectors. The AAV may be a hybrid AAV vector having a capsid protein (e.g., any one or more of AAV serotypes 1-12 and others) and genome (e.g., AAV serotype 2) from different AAV. An AAV vector is preferred, in particular AAV5. Particularly preferred is a liver-directed vector (e.g. a liver-directed AAV vector), although a muscle-directed vector may also be useful.

In a particular embodiment of the present invention, methods are provided for the administration of a viral vector comprising a nucleic acid sequence encoding a Factor IX variant polypeptide (or a molecule comprising the same) or a functional fragment thereof. As described herein, expression of a variant polypeptide following administration of such an adenoviral vector may improve the Factor IX activity.

Cells

Another aspect of the invention includes a cell comprising the nucleic acid or vector of the invention.

The cell may be of human origin. The cell may be a platelet, a T cell, or a hematopoietic cell, etc. The cell may be autologous or allogeneic with respect to the subject to be treated. The cell may be modified ex vivo, e.g., by incorporating a nucleic acid into a genomic location operatively linked with a promoter sequence, so as to express a Factor IX variant polypeptide of the invention in the cell. AAV vectors may be used for this purpose. The cells may also be cultured (expanded) in vitro. Suitable methods are known to the skilled person in the art.

Pharmaceutical Compositions

The invention provides a pharmaceutical composition comprising a Factor IX variant polypeptide, a molecule comprising the same, a nucleic acid, vector or cell as described above. The composition may be for administration to a subject, such as an animal, typically a human subject.

The composition is pharmaceutically acceptable and will typically include a suitable carrier. A thorough discussion of pharmaceutically acceptable carriers is available in reference 21. The composition may be sterile, pyrogen- and/or preservative-free.

The Factor IX variant polypeptide in the composition may be lyophilized. The lyophilized polypeptide may be for reconstitution with liquid diluent, e.g. sterile water for injection. Typical excipients in a composition comprising lyophilized Factor IX variant polypeptide include tri-sodium citrate dihydrate, polysorbate 80, mannitol, sucrose, and/or HCl.

Non-lyophilized Factor IX variant polypeptide may be provided in buffered liquid form, e.g. in a citrate buffer, optionally containing a stabiliser and/or a bulking agent.

The composition may be for intravenous administration. Other routes of administration include the intramuscular, oral, topical or parenteral route.

Compositions may be prophylactic (to prevent bleeding) or therapeutic (to treat bleeding).

Methods of Treatment

The invention also provides the Factor IX variant, molecule comprising the same, nucleic acid, vector, cell or pharmaceutical composition as described herein for use as a medicament.

For example, the invention provides a method for the treatment or prophylaxis of a blood coagulation disorder in a subject in a patient in need thereof comprising administering a therapeutically effective amount of the Factor IX variant (or a molecule comprising the Factor IX variant, a nucleic acid molecule encoding the Factor IX variant, etc.) to the subject.

The blood coagulation disorder may be a Factor IX deficiency, for example hemophilia B.

Such methods have efficacy in the prophylaxis or treatment of disorders where pro-coagulant is needed (e.g., to prevent, reduce or inhibit bleeding) and include, without limitation, hemophilia, particularly hemophilia B. The invention therefore provides a method for the treatment or prophylaxis of a blood coagulation disorder in a subject, in particular the treatment or prophylaxis of bleeding in patients with hemophilia B (congenital factor IX deficiency)
.

By a "therapeutically effective amount" it is meant that the administration of that amount (e.g. of a Factor IX variant polypeptide of the invention) to an individual, either in a single dose or as part of a series, is effective for treatment or prevention.

The invention also provides the Factor IX variant (or a molecule comprising the Factor IX variant, a nucleic acid molecule encoding the Factor IX variant, etc.) for use in the treatment or prophylaxis of a blood coagulation disorder in a subject, in particular the treatment or prophylaxis of bleeding in patients with hemophilia B.

Also provided is the use of the Factor IX variant (or a molecule comprising the Factor IX variant, a nucleic acid molecule encoding the Factor IX variant, etc.) for the manufacture of a medicament for the treatment or prophylaxis of a blood coagulation disorder in a subject, in particular the treatment or prophylaxis of bleeding in patients with hemophilia B.

More generally, disorders that may benefit from this invention are bleeding disorders including hemophilia (hemophilia A, hemophilia B, hemophilia A and B patients with inhibitory antibodies; in particular hemophilia B), deficiencies in at least one coagulation factor (e.g., Factors VII, IX, X, XI, V, XII, II, and/or von Willebrand factor; in particular Factor IX), combined FV/FVIII deficiency, vitamin K epoxide reductase CI deficiency, gamma-carboxylase deficiency; bleeding associated with trauma, injury, thrombosis, thrombocytopenia, stroke, coagulopathy (hypocoagulability), disseminated intravascular coagulation (DIC); over-anticoagulation associated with heparin, low molecular weight heparin, pentasaccharide, warfarin, small molecule antithrombotics (i.e. FXa inhibitors); and platelet disorders such as, Bernard Soulier syndrome, Glanzman thromblastemia, and storage pool deficiency.

In a particular embodiment, the disorder is hemophilia B.

The terms "treatment", "therapy" and "treating" may include prophylaxis, unless indicated otherwise. A disorder is treated or prevented if administration of a compound or composition of the invention (e.g. a Factor IX variant polypeptide) to a subject (e.g. a human with Factor IX deficiency such as hemophilia B) results in a therapeutic or prophylactic effect. This means that the plasma level of Factor IX activity in the subject is increased following treatment, at least temporarily, when measured with at least one Factor IX assay. The Factor IX activity is typically determined using an in vitro aPTT-based one stage clotting assay (e.g. as described in Example 3). The increase may be clinically relevant, e.g. a reduction in the frequency or intensity of bleeding events.

One way of expressing Factor IX activity in plasma is as a percentage relative to normal human plasma. Another way of expressing Factor IX activity in plasma is in International Units (IU) relative to an International Standard for Factor IX in plasma. One IU of Factor IX activity is equivalent to that quantity of Factor IX in one ml of normal human plasma.

One way of checking efficacy of prophylaxis or treatment is by measuring the plasma Factor IX activity in the subject after prophylaxis or treatment, and comparing it to the plasma Factor IX activity in that subject before prophylaxis or treatment. An increase in Factor IX activity after prophylaxis or treatment (e.g. from <1%, or 1%-5%, or 5-40% of normal human plasma to e.g., >40%, >50%, or >60% peak levels of normal human plasma) indicates a prophylactic or therapeutic effect. Factor IX levels of 5-10% of normal human serum have been targeted in clinical trials for achieving bleeding control while on prophylaxis.

A prophylactic or therapeutic effect is also achieved where the Factor IX activity after prophylaxis or treatment is sufficient to prevent, reduce or inhibit bleeding.

The Factor IX activity after prophylaxis or treatment may be outside of the pathological range (e.g. >40% peak levels of normal human serum). The Factor IX activity after prophylaxis or treatment may be comparable to the Factor IX activity in normal human plasma.

Factor IX activity can be measured using any Factor IX activity assay known to the skilled person, for example using an aPTT assay (a decrease in aPTT value indicates increased Factor IX activity). In a preferred embodiment therefore Factor IX activity is determined using an in vitro aPTT-based one stage clotting assay, e.g. as described in Example 3.

A Factor IX variant polypeptide according to the invention may have a higher specific molar activity when administered in vivo to a subject than the corresponding wild-type Factor IX polypeptide. For example, the % increase in plasma Factor IX activity (e.g. measured using an in vitro aPTT-based one stage clotting assay) may be higher when using a Factor IX variant polypeptide of the invention as compared with using the same molar amount of the corresponding wild-type Factor IX polypeptide. Another way of describing this is that the aPTT time when using a Factor IX variant polypeptide of the invention is shorter as compared with using the same molar amount of the corresponding wild-type Factor IX polypeptide.

Effective initial doses of Factor IX variant polypeptide can be established. The required dose for on demand treatment is determined using the following formulae:

Required dose (International Units, IU)=body weight (kg)×desired Factor IX rise (% of normal or IU/dl)×{reciprocal of observed recovery (IU/kg per IU/dl)}

Expected factor IX rise (IU/dl or % of normal)= Dose (IU)×Recovery (IU/dl per IU/kg)/body weight (kg)

The initial dose is adjusted based on the patient's clinical condition and response.

For determination of an adequate maintenance dose any extended half-life of the Factor IX variant polypeptide is taken into account. A typical regimen for routine prophylaxis to prevent bleeding in patients with hemophilia B is 35 to 50 μl/kg once weekly. Some patients who are well-controlled on a once-weekly regimen might be treated with up to 75 μl/kg on an interval of 10 or 14 days.

The exact dosage and duration of treatment will depend on the severity of the Factor IX deficiency, the location and extent of bleeding, and the patient's clinical condition, age and recovery of Factor IX.

The methods of treatment or prevention described herein include the administration of a viral vector comprising a nucleic acid sequence encoding a Factor IX variant polypeptide (or a molecule comprising the same), for example for use in gene therapy. A preferred vector is an adenovirus-associated vector, e.g. AAV5. A lentiviral vector can also be used.

Treatment or prevention may also be achieved using gene editing approaches, for example using zinc finger nucleases or CRISPR (e.g. CRISPR/Cas9). Such approaches may replace defective Factor IX gene with a nucleic acid encoding the functional Factor IX variant polypeptide of the invention, using methods that are known to the skilled person in the art (e.g. reference 22). Another approach is to insert a nucleic acid encoding the Factor IX variant polypeptide of the invention into the albumin locus to ensure long-term expression of Factor IX despite hepatocyte cell division, using methods known in the art (e.g. references 23, 24 or 25).

The methods of treatment or prevention described herein also include the administration of cells (e.g., platelets, T cells, hematopoietic cells, etc.) to a subject wherein the cells express the Factor IX variant polypeptide of the invention, or wherein the cells express a molecule comprising the Factor IX variant polypeptide of the invention. The cells may be autologous or allogeneic relative to the subject to be treated.

General

The practice of the present invention will employ, unless otherwise indicated, conventional methods of chemistry, biochemistry, molecular biology, immunology and pharmacology, within the skill of the art. Such techniques are explained fully in the literature. See, e.g., references 26-32, etc.

The term "comprising" encompasses "including" as well as "consisting" e.g. a composition "comprising" X may consist exclusively of X or may include something additional e.g. X+Y.

The term "about" in relation to a numerical value x is optional and means, for example, x±10%.

References to a percentage sequence identity between two amino acid sequences means that, when aligned, that percentage of amino acids are the same in comparing the two sequences. This alignment and the percent homology or sequence identity can be determined using software programs known in the art, for example those described in section 7.7.18 of ref.

33. A preferred alignment is determined by the Smith-Waterman homology search algorithm using an affine gap search with a gap open penalty of 12 and a gap extension penalty of 2, BLOSUM matrix of 62. The Smith-Waterman homology search algorithm is disclosed in ref. 34.

The word "substantially" does not exclude "completely" e.g. a composition which is "substantially free" from Y may be completely free from Y. Where necessary, the word "substantially" may be omitted from the definition of the invention.

All publications, patents, and patent applications disclosed herein are incorporated by reference to the same extent as if each individual publication, patent or patent application was specifically and individually indicated to be incorporated by reference.

The following examples are provided to illustrate various embodiments of the present invention. The examples are illustrative and are not intended to limit the invention in any way.

EXAMPLES

A series of exemplary recombinant FIX variant polypeptides were produced by mutating one or two amino acid positions in human wild-type FIX polypeptide (SEQ ID NO:

1) fused with a recombinant mature human albumin via a cleavable linker (IDELVION®/albutrepenonacog alfa, SEQ ID NO: 10). The recombinant FIX variants were expressed in HEK cells and the cell culture supernatant or purified proteins tested for activity and antigen. The activity to antigen ratios were compared to the corresponding polypeptide comprising wild-type FIX. FIX variants having certain mutations at positions 410 and 338 of wild-type FIX showed a surprisingly high activity, as demonstrated below.

Example 1

Generation of Plasmid DNA, Cell Transfection and Protein Expression

Plasmid DNA encoding Factor IX or Factor IX-albumin fusion polypeptides (FIX-FP) comprising either wild-type or variant FIX were generated according to standard techniques in the art. The mature wild-type Factor IX polypeptide sequence is shown in SEQ ID NO: 1. Exemplary Factor IX variant polypeptide sequences are shown in SEQ ID NO: 11-14. In particular, E (glutamic acid) at position 410 of wild-type Factor IX (SEQ ID NO: 1) was substituted with H (histidine) or K (lysine), and/or R (arginine) at position 338 of wild-type Factor IX (SEQ ID NO: 1) was substituted with V (valine), W (tryptophan), T (threonine), or L (lysine). Single and double mutants with mutations at positions 338 and/or 410 were generated. The linker and albumin of the Factor IX-FP were as defined in SEQ ID NOs 8 and 9, respectively. However, other linkers and half-life enhancing portions can be used (as described in, e.g., reference 1), or they can be omitted.

Plasmid DNA was cloned in pcDNA3.1 vector and amplified in E. coli XL10-Gold Ultracompetent Cells (Agiland Technologies Cat No.:200315). Plasmid DNA was purified using standard protocols (QIAGEN Plasmid Plus Purification Cat No.: 12945, Hilden, Germany). Transient production of polypeptides was commenced in 250 ml scale, with the Expi293F expression kit (Cat. No. A14635, ThermoFisher). Viable Expi293™ cells in exponential growth phase were collected and re-suspended accordingly to obtain a starting cell density of $2.5 \times 10^6$ cells/ml in 2 L shaker flasks (Corning, Lowell, MA). Separately, plasmid DNA (125 µg) and Expifectamin™ 293 reagent (675 µl) were diluted in 12.5 ml Opti-MEM® I Reduced serum medium. Diluted Expifectamin™ 293 reagent and plasmid DNA were mixed in equal parts. The complex was added to 225 ml of $62.5 \times 10^7$ total viable cells in Expi293™ Expression medium. Expression medium was supplemented with 50 µg/ml Menadione K3 (Sigma Aldrich, Steinheim, Germany). Culture was incubated in an orbital shaker incubator at 37° C. (8% $CO_2$, 150 rpm). After 17-20 hours, Enhancer I (1.25 ml) and Enhancer II (12.5 ml), which are part of the Expi293 Expression kit, were added to the culture. After a total culture time of 96 hours, the culture supernatant was harvested using appropriate sterile filter. Factor IX protein was then purified as explained in Example 2.

For experiments that used cell culture supernatants to measure Factor IX activity etc., the FIX-FP wild-type and FIX-FP variant polypeptides were expressed as described above, except that the culture volume was 50 ml and the culture supernatant from the transfected cells was collected at 48 hours. Factor IX activity was assessed in a one stage Factor IX specific clotting assay and antigen levels were determined with a Factor IX specific ELISA, as described below (Examples 3 and 4).

Example 2

Protein Purification

Cell culture supernatants containing Factor IX albumin fusion polypeptide, respective Factor IX polypeptide, as described in Example 1 above were applied on a Poros 50HQ column previously equilibrated with 20 mM Hepes, 50 mM NaCl and 12 mmol EDTA buffer pH 6.2. Subsequently, the column was washed with buffer containing 20 mM Hepes, 100 mM NaCl pH 6.2. Elution of the bound FIX fusion polypeptide was achieved by adding 10 mmol $CaCl_2$ to the washing buffer.

Example 3

Determination of Factor IX Activity and Antigen

Factor IX activity was determined as clotting or coagulation activity (FIX:C) using commercially available aPTT reagents (Pathromtin® SL and FIX depleted plasma, Siemens Healthcare). An internal substandard calibrated against the WHO International FIX concentrate Standard was used as a reference.

Factor IX antigen (FIX:Ag) was determined by an ELISA according to standard protocols known to those skilled in the art. Briefly, microtiter plates were incubated with 1004 per well of the capture antibody (Paired antibodies for Factor IX ELISA (CL20041K), Cedarlane, but other sources of appropriate antibodies may also be applied) overnight at ambient temperature. After washing plates three times with washing buffer B (Sigma T9039) each well was incubated with 200 µL blocking buffer C (Sigma P3688) for one hour at ambient temperature. After another three wash steps with buffer B, serial dilutions of the test sample in buffer B as well as serial dilutions of a substandard (SHP) in buffer B (volumes per well: 100 µL) were incubated for 90 min. at ambient temperature. After three wash steps with buffer B, 100 mL of a 1:200 dilution of the detection antibody (Paired antibodies for Factor IX ELISA, peroxidase labelled, Cedarlane) in buffer B, were added to each well and incubated for another 90 min at ambient temperature. After three wash steps with buffer B, 100 µL of substrate solution (TMB, Siemens Healthcare, OUVF) were added per well and incubated for 30 minutes at ambient temperature in the dark. Addition of 100 µL undiluted stop solution (Siemens Healthcare, OSFA) prepared the samples for reading in a suitable microplate reader at 450 nm wavelength. Concentrations of test samples were then calculated using the standard curve with standard human plasma as reference.

Example 4

Comparison of Factor IX-Activity/Factor IX-Antigen Ratio of Factor IX Variants Relative to Wildtype Factor IX activity and antigen were performed as described in Example 3 above. Factor IX variant specific activity was normalized to Factor IX antigen levels, measured via anti-Factor IX ELISA (ratio of FIX:C to FIX:Ag) to control for experimental variation, thereby representing a measure that is directly proportional to the molar specific activity of the different constructs. The resulting activity of wild-type Factor IX (in this example, IDELVION®, SEQ ID NO: 10) was assigned the value '1'. The activity of the Factor IX variants based on IDELVION® are indicated relative to the activity of wild-type Factor IX (IDELVION®).

Tables 1 and 2 below show the specific activity of various FIX-FP variants relative to wild-type FIX-FP, measured using cell culture supernatants containing the recombinantly expressed proteins (Table 1) or using purified protein (Table 2, 3 and 4).

TABLE 1

Specific activities of Factor IX variants relative to wild-type Factor IX (Idelvion ®, measured using supernatants.

| Construct | Specific activity relative to wild-type FIX-FP |
|---|---|
| FIX-FP Control (wild-type) | 1.00 |
| FIX-FP R338V + E410H | 7.77 |
| FIX-FP R338T + E410H | 6.75 |
| FIX-FP R338W + E410H | 5.32 |
| FIX-FP R338L + E410K | 5.58 |
| FIX-FP E410H | 2.03 |
| FIX-FP R338V | 4.26 |
| FIX-FP R338L | 4.76 |
| FIX-FP R338T | 2.55 |

TABLE 2

Specific activities of Factor IX variants relative to wild-type Factor IX, measured using purified supernatants (anionic exchange).

| Construct | Specific activity relative to wild-type FIX-FP |
|---|---|
| FIX-FP Control (wild-type) | 1.00 |
| FIX-FP R338V + E410H | 7.47 |
| FIX-FP R338T + E410H | 6.68 |
| FIX-FP R338W + E410H | 4.02 |
| FIX-FP R338L + E410K | 5.48 |
| FIX-FP E410H | 3.38 |
| FIX-FP R338V | 3.15 |
| FIX-FP R338L | 4.59 |

Tables 1 and 2 show that FIX-FP variants with certain mutations at positions 338 and/or 410 of wild-type Factor IX yielded greater specific activity than wild-type FIX-FP. Furthermore, double mutants with certain mutations at positions 338 and 410 of wild-type Factor IX (e.g. R338V+ E410H, R338V+E410T) yielded greater specific activity than both the wild-type FIX-FP and each of the respective single mutants (e.g. R338V, R338T, E410H). Indeed, the activity of the double mutants can be more than additive (synergistic) relative to the respective single mutants. Additionally, the specific activity of the R338V+E410H, R338T+ E410H and R338W+E410H double mutants was higher than the activity of the variant which corresponds to the Factor IX "Padua" mutant, R338L, see reference 35. The specific activity of the R338V+E410H and R338T+E410H double mutants was furthermore higher than the activity of the variant which corresponds to the "Padua" R338L+E410K double mutant.

In a further experiment, the specific activity of the R338L+E410K and R338L+E410H double mutants produced as described above was determined and compared to the activity of the corresponding R338L single mutant. Table 3 below shows that the R338L+E410H double mutant has a higher specific activity than the R338L single mutant, which itself has a higher specific activity compared to wild-type (as shown in Tables 1 and 2 above). The R338L+E410H double mutant is therefore another useful Factor IX variant.

TABLE 3

Specific activities of FIX-FP variants relative to R338L, measured using supernatants.

| Construct | Specific activity relative to R338L |
|---|---|
| FIX-FP Control (R338L) | 1.00 |
| FIX-FP R338L + E410H | 2.10 |
| FIX-FP R338L + E410K | 1.34 |

Furthermore, Table 3 shows that the E410H mutation, when incorporated into a double mutant, results in an overall higher activity than the E410K mutation in the same double mutants. It will be understood by the skilled person that the invention has been described by way of example only and modifications may be made whilst remaining within the scope and spirit of the invention.

TABLE 4

Comparison of specific activities of Factor IX variants, relative to wildtype Factor IX measured using purified supernatants (anionic exchange).

| Construct | Specific activity relative to wt-FIX |
|---|---|
| Control FIX-wildtype | 1.0 |
| FIX R338V + E410H | 6.48 |
| FIX R338T + E410H | 8.01 |

Table 4 shows, that the specific activity of the double mutants R338V+E410H and R338T+E410H expressed as Factor IX which is not fused to albumin is also higher than the Factor IX wildtype control. Thus, the improved specific activity of the Factor IX mutations of the invention is independent from the albumin fusion.

REFERENCES

[1] WO 2007/144173
[2] Beattie & Dugaiczyk (1982) Gene 20:415-422
[3] WO 2005/024044
[4] Lichenstein et al. (1994) J. Biol. Chem. 269:18149-18154
[5] Cooke & David (1985) J. Clin. Invest. 76:2420-2424
[6] WO 2005/001025
[7] Powell et al. (2013) N. Engl. J. Med., 369:2313-2323

[8] Peters et al. (2010) Blood 115:2057-2064
[9] Shapiro et al. (2012) Blood 119:666-672
[10] Fares et al. (1992) Proc Natl Acad Sci USA 15; 89(10):4304-4308
[11] Calo et al. (2015) Precision Medicine, 2, e989
[12] WO 2011/004361
[13] Schellenberger et al. (2009) Nature Biotechnology 27, 1186-1190
[14] WO 2017/024060
[15] WO 2012/006624
[16] WO 2015/106052
[17] Collins et al. (2014) Blood 124:3880-3886
[18] WO 2006/127896
[19] WO 2005/055950
[20] DeFrees et al. (2006) Glycobiology 16(9):833-843
[21] Gennaro (2000) Remington: The Science and Practice of Pharmacy. 20th edition, ISBN: 0683306472.
[22] Qiang Wang et al. (2017) Blood December 2017, 130 (Suppl 1), 5562
[23] Anguela et al. (2013) Blood 122, 3283-3287
[24] Sharma et al. (2015) Blood 126, 1777-1784
[25] Barzel et al. (2015) Nature 517, 360-364
[26] Methods In Enzymology (S. Colowick and N. Kaplan, eds., Academic Press, Inc.)
[27] Handbook of Experimental Immunology, Vols. I-IV (D. M. Weir and C. C. Blackwell, eds, 1986, Blackwell Scientific Publications)
[28] Sambrook et al. (2001) Molecular Cloning: A Laboratory Manual, 3rd edition (Cold Spring Harbor Laboratory Press)
[29] Handbook of Surface and Colloidal Chemistry (Birdi, K. S. ed., CRC Press, 1997)
[30] Ausubel et al. (eds) (2002) Short protocols in molecular biology, 5th edition (Current Protocols).
[31] Molecular Biology Techniques: An Intensive Laboratory Course, (Ream et al., eds., 1998, Academic Press)
[32] PCR (Introduction to Biotechniques Series), 2nd ed. (Newton & Graham eds., 1997, Springer Verlag)
[33] Current Protocols in Molecular Biology (F. M. Ausubel et al., eds., 1987) Supplement 30
[34] Smith & Waterman (1981) Adv. Appl. Math. 2: 482-489
[35] Simioni et al. (2009) N Engl J Med. October 22; 361(17):1671-1675

SEQUENCE LISTING
>Human wild-type FIX polypeptide
SEQ ID NO: 1
YNSGKLEEFVQGNLERECMEEKCSFEEAREVFENTERTTEFWKQYVDGDQCESNPCLNG

GSCKDDINSYECWCPFGFEGKNCELDVTCNIKNGRCEQFCKNSADNKVVCSCTEGYRLAE

NQKSCEPAVPFPCGRVSVSQTSKLTRAETVFPDVDYVNSTEAETILDNITQSTQSFNDFTRV

VGGEDAKPGQFPWQVVLNGKVDAFCGGSIVNEKWIVTAAHCVETGVKITVVAGEHNIEETE

HTEQKRNVIRIIPHHNYNAAINKYNHDIALLELDEPLVLNSYVTPICIADKEYTNIFLKFGSGYV

SGWGRVFHKGRSALVLQYLRVPLVDRATCLRSTKFTIYNNMFCAGFHEGGRDSCQGDSGG

PHVTEVEGTSFLTGIISWGEECAMKGKYGIYTKVSRYVNWIKEKTKLT

>Coding sequence for human wild-type FIX polypeptide
SEQ ID NO: 2
ATGTATAATTCAGGTAAATTGGAAGAGTTTGTTCAAGGGAACCTTGAGAGAGAATGTATG

GAAGAAAGTGTAGTTTTGAAGAAGCACGAGAAGTTTTTGAAAACACTGAAAGAACAACT

GAATTTTGGAAGCAGTATGTTGATGGAGATCAGTGTGAGTCCAATCCATGTTTAAATGGC

GGCAGTTGCAAGGATGACATTAATTCCTATGAATGTTGGTGTCCCTTTGGATTTGAAGGA

AAGAACTGTGAATTAGATGTAACATGTAACATTAAGAATGGCAGATGCGAGCAGTTTTGT

AAAAATAGTGCTGATAACAAGGTGGTTTGCTCCTGTACTGAGGGATATCGACTTGCAGA

AAACCAGAAGTCCTGTGAACCAGCAGTGCCATTTCCATGTGGAAGAGTTTCTGTTTCAC

AAACTTCTAAGCTCACCCGTGCTGAGACTGTTTTTCCTGATGTGGACTATGTAAATTCTA

CTGAAGCTGAAACCATTTTGGATAACATCACTCAAAGCACCCAATCATTTAATGACTTCA

CTCGGGTTGTTGGTGGAGAAGATGCCAAACCAGGTCAATTCCCTTGGCAGGTTGTTTTG

AATGGTAAAGTTGATGCATTCTGTGGAGGCTCTATCGTTAATGAAAAATGGATTGTAACT

GCTGCCCACTGTGTTGAAACTGGTGTTAAAATTACAGTTGTCGCAGGTGAACATAATATT

GAGGAGACAGAACATACAGAGCAAAAGCGAAATGTGATTCGAATTATTCCTCACCACAA

CTACAATGCAGCTATTAATAAGTACAACCATGACATTGCCCTTCTGGAACTGGACGAACC

CTTAGTGCTAAACAGCTACGTTACACCTATTTGCATTGCTGACAAGGAATACACGAACAT

CTTCCTCAAATTTGGATCTGGCTATGTAAGTGGCTGGGGAAGAGTCTTCCACAAAGGGA

GATCAGCTTTAGTTCTTCAGTACCTTAGAGTTCCACTTGTTGACCGAGCCACATGTCTTC

GATCTACAAAGTTCACCATCTATAACAACATGTTCTGTGCTGGCTTCCATGAAGGAGGTA

GAGATTCATGTCAAGGAGATAGTGGGGGACCCCATGTTACTGAAGTGGAAGGGACCAG

TTTCTTAACTGGAATTATTAGCTGGGGTGAAGAGTGTGCAATGAAAGGCAAATATGGAAT

ATATACCAAGGTATCCCGGTATGTCAACTGGATTAAGGAAAAAACAAAGCTCACTTAA

>Human wild-type FIX polypeptide including signal peptide
and propeptide
                                                    SEQ ID NO: 3
MQRVNMIMAESPGLITICLLGYLLSAECTVFLDHENANKILNRPKRYNSGKLEEFVQGNLERE

CMEEKCSFEEAREVFENTERTTEFWKQYVDGDQCESNPCLNGGSCKDDINSYECWCPFG

FEGKNCELDVTCNIKNGRCEQFCKNSADNKVVCSCTEGYRLAENQKSCEPAVPFPCGRVS

VSQTSKLTRAETVFPDVDYVNSTEAETILDNITQSTQSFNDFTRVVGGEDAKPGQFPWQVV

LNGKVDAFCGGSIVNEKWIVTAAHCVETGVKITVVAGEHNIEETEHTEQKRNVIRIIPHHNYN

AAINKYNHDIALLELDEPLVLNSYVTPICIADKEYTNIFLKFGSGYVSGWGRVFHKGRSALVLQ

YLRVPLVDRATCLRSTKFTIYNNMFCAGFHEGGRDSCQGDSGGPHVTEVEGTSFLTGIISW

GEECAMKGKYGIYTKVSRYVNWIKEKTKLT

>Coding sequence for human wild-type FIX polypeptide
including signal peptide and propeptide
                                                    SEQ ID NO: 4
ATGCAGCGCGTGAACATGATCATGGCAGAATCACCAGGCCTCATCACCATCTGCCTTTT

AGGATATCTACTCAGTGCTGAATGTACAGTTTTTCTTGATCATGAAAACGCCAACAAAAT

TCTGAATCGGCCAAAGAGGTATAATTCAGGTAAATTGGAAGAGTTTGTTCAAGGGAACC

TTGAGAGAGAATGTATGGAAGAAAGTGTAGTTTTGAAGAAGCACGAGAAGTTTTTGAAA

ACACTGAAAGAACAACTGAATTTTGGAAGCAGTATGTTGATGGAGATCAGTGTGAGTCC

AATCCATGTTTAAATGGCGGCAGTTGCAAGGATGACATTAATTCCTATGAATGTTGGTGT

CCCTTTGGATTTGAAGGAAAGAACTGTGAATTAGATGTAACATGTAACATTAAGAATGGC

AGATGCGAGCAGTTTTGTAAAAATAGTGCTGATAACAAGGTGGTTTGCTCCTGTACTGA

GGGATATCGACTTGCAGAAAACCAGAAGTCCTGTGAACCAGCAGTGCCATTTCCATGTG

GAAGAGTTTCTGTTTCACAAACTTCTAAGCTCACCCGTGCTGAGACTGTTTTTCCTGATG

TGGACTATGTAAATTCTACTGAAGCTGAAACCATTTTGGATAACATCACTCAAAGCACCC

-continued

AATCATTTAATGACTTCACTCGGGTTGTTGGTGGAGAAGATGCCAAACCAGGTCAATTC

CCTTGGCAGGTTGTTTTGAATGGTAAAGTTGATGCATTCTGTGGAGGCTCTATCGTTAAT

GAAAAATGGATTGTAACTGCTGCCCACTGTGTTGAAACTGGTGTTAAAATTACAGTTGTC

GCAGGTGAACATAATATTGAGGAGACAGAACATACAGAGCAAAAGCGAAATGTGATTCG

AATTATTCCTCACCACAACTACAATGCAGCTATTAATAAGTACAACCATGACATTGCCCTT

CTGGAACTGGACGAACCCTTAGTGCTAAACAGCTACGTTACACCTATTTGCATTGCTGA

CAAGGAATACACGAACATCTTCCTCAAATTTGGATCTGGCTATGTAAGTGGCTGGGGAA

GAGTCTTCCACAAAGGGAGATCAGCTTTAGTTCTTCAGTACCTTAGAGTTCCACTTGTTG

ACCGAGCCACATGTCTTCGATCTACAAAGTTCACCATCTATAACAACATGTTCTGTGCTG

GCTTCCATGAAGGAGGTAGAGATTCATGTCAAGGAGATAGTGGGGGACCCCATGTTACT

GAAGTGGAAGGGACCAGTTTCTTAACTGGAATTATTAGCTGGGGTGAAGAGTGTGCAAT

GAAAGGCAAATATGGAATATATACCAAGGTATCCCGGTATGTCAACTGGATTAAGGAAA

AAACAAAGCTCACTTAA

>Human wild-type FIXa light chain polypeptide
　　　　　　　　　　　　　　　　　　　　　　　　　　SEQ ID NO: 5
YNSGKLEEFVQGNLERECMEEKCSFEEAREVFENTERTTEFWKQYVDGDQCESNPCLNG

GSCKDDINSYECWCPFGFEGKNCELDVTCNIKNGRCEQFCKNSADNKVVCSCTEGYRLAE

NQKSCEPAVPFPCGRVSVSQTSKLTR

>Human wild-type FIXa heavy chain polypeptide
　　　　　　　　　　　　　　　　　　　　　　　　　　SEQ ID NO: 6
VVGGEDAKPGQFPWQVVLNGKVDAFCGGSIVNEKWIVTAAHCVETGVKITVVAGEHNIEET

EHTEQKRNVIRIIPHHNYNAAINKYNHDIALLELDEPLVLNSYVTPICIADKEYTNIFLKFGSGY

VSGWGRVFHKGRSALVLQYLRVPLVDRATCLRSTKFTIYNNMFCAGFHEGGRDSCQGDSG

GPHVTEVEGTSFLTGIISWGEECAMKGKYGIYTKVSRYVNWIKEKTKLT

>Human wild-type FIX polypeptide T148A polymorphic variant
　　　　　　　　　　　　　　　　　　　　　　　　　　SEQ ID NO: 7
YNSGKLEEFVQGNLERECMEEKCSFEEAREVFENTERTTEFWKQYVDGDQCESNPCLNG

GSCKDDINSYECWCPFGFEGKNCELDVTCNIKNGRCEQFCKNSADNKVVCSCTEGYRLAE

NQKSCEPAVPFPCGRVSVSQTSKLTRAEAVFPDVDYVNSTEAETILDNITQSTQSFNDFTRV

VGGEDAKPGQFPWQVVLNGKVDAFCGGSIVNEKWIVTAAHCVETGVKITVVAGEHNIEETE

HTEQKRNVIRIIPHHNYNAAINKYNHDIALLELDEPLVLNSYVTPICIADKEYTNIFLKFGSGYV

SGWGRVFHKGRSALVLQYLRVPLVDRATCLRSTKFTIYNNMFCAGFHEGGRDSCQGDSGG

PHVTEVEGTSFLTGIISWGEECAMKGKYGIYTKVSRYVNWIKEKTKLT

>Linker
　　　　　　　　　　　　　　　　　　　　　　　　　　SEQ ID NO: 8
PVSQTSKLTRAETVFPDV

>Mature human albumin
　　　　　　　　　　　　　　　　　　　　　　　　　　SEQ ID NO: 9
DAHKSEVAHRFKDLGEENFKALVLIAFAQYLQQCPFEDHVKLVNEVTEFAKTCVADESAEN

CDKSLHTLFGDKLCTVATLRETYGEMADCCAKQEPERNECFLQHKDDNPNLPRLVRPEVD

VMCTAFHDNEETFLKKYLYEIARRHPYFYAPELLFFAKRYKAAFTECCQAADKAACLLPKLD

ELRDEGKASSAKQRLKCASLQKFGERAFKAWAVARLSQRFPKAEFAEVSKLVTDLTKVHTE

CCHGDLLECADDRADLAKYICENQDSISSKLKECCEKPLLEKSHCIAEVENDEMPADLPSLA

ADFVESKDVCKNYAEAKDVFLGMFLYEYARRHPDYSVVLLLRLAKTYETTLEKCCAAADPH

ECYAKVFDEFKPLVEEPQNLIKQNCELFEQLGEYKFQNALLVRYTKKVPQVSTPTLVEVSRN

LGKVGSKCCKHPEAKRMPCAEDYLSVVLNQLCVLHEKTPVSDRVTKCCTESLVNRRPCFS

-continued

ALEVDETYVPKEFNAETFTFHADICTLSEKERQIKKQTALVELVKHKPKATKEQLKAVMDDFA

AFVEKCCKADDKETCFAEEGKKLVAASQAALGL

>FIX (wild-type) albumin fusion

SEQ ID NO: 10
YNSGKLEEFVQGNLERECMEEKCSFEEAREVFENTERTTEFWKQYVDGDQCESNPCLNG

GSCKDDINSYECWCPFGFEGKNCELDVTCNIKNGRCEQFCKNSADNKVVCSCTEGYRLAE

NQKSCEPAVPFPCGRVSVSQTSKLTRAETVFPDVDYVNSTEAETILDNITQSTQSFNDFTRV

VGGEDAKPGQFPWQVVLNGKVDAFCGGSIVNEKWIVTAAHCVETGVKITVVAGEHNIEETE

HTEQKRNVIRIIPHHNYNAAINKYNHDIALLELDEPLVLNSYVTPICIADKEYTNIFLKFGSGYV

SGWGRVFHKGRSALVLQYLRVPLVDRATCLRSTKFTIYNNMFCAGFHEGGRDSCQGDSGG

PHVTEVEGTSFLTGIISWGEECAMKGKYGIYTKVSRYVNWIKEKTKLTPVSQTSKLTRAETVF

PDVDAHKSEVAHRFKDLGEENFKALVLIAFAQYLQQCPFEDHVKLVNEVTEFAKTCVADESA

ENCDKSLHTLFGDKLCTVATLRETYGEMADCCAKQEPERNECFLQHKDDNPNLPRLVRPE

VDVMCTAFHDNEETFLKKYLYEIARRHPYFYAPELLFFAKRYKAAFTECCQAADKAACLLPK

LDELRDEGKASSAKQRLKCASLQKFGERAFKAWAVARLSQRFPKAEFAEVSKLVTDLTKVH

TECCHGDLLECADDRADLAKYICENQDSISSKLKECCEKPLLEKSHCIAEVENDEMPADLPS

LAADFVESKDVCKNYAEAKDVFLGMFLYEYARRHPDYSVVLLLRLAKTYETTLEKCCAAADP

HECYAKVFDEFKPLVEEPQNLIKQNCELFEQLGEYKFQNALLVRYTKKVPQVSTPTLVEVSR

NLGKVGSKCCKHPEAKRMPCAEDYLSVVLNQLCVLHEKTPVSDRVTKCCTESLVNRRPCF

SALEVDETYVPKEFNAETFTFHADICTLSEKERQIKKQTALVELVKHKPKATKEQLKAVMDDF

AAFVEKCCKADDKETCFAEEGKKLVAASQAALGL

>FIX variant R338V/E410H

SEQ ID NO: 11
YNSGKLEEFVQGNLERECMEEKCSFEEAREVFENTERTTEFWKQYVDGDQCESNPCLNG

GSCKDDINSYECWCPFGFEGKNCELDVTCNIKNGRCEQFCKNSADNKVVCSCTEGYRLAE

NQKSCEPAVPFPCGRVSVSQTSKLTRAETVFPDVDYVNSTEAETILDNITQSTQSFNDFTRV

VGGEDAKPGQFPWQVVLNGKVDAFCGGSIVNEKWIVTAAHCVETGVKITVVAGEHNIEETE

HTEQKRNVIRIIPHHNYNAAINKYNHDIALLELDEPLVLNSYVTPICIADKEYTNIFLKFGSGYV

SGWGRVFHKGRSALVLQYLRVPLVDRATCLVSTKFTIYNNMFCAGFHEGGRDSCQGDSGG

PHVTEVEGTSFLTGIISWGEECAMKGKYGIYTKVSRYVNWIKHKTKLT

>FIX variant R338L/E410H

SEQ ID NO: 12
YNSGKLEEFVQGNLERECMEEKCSFEEAREVFENTERTTEFWKQYVDGDQCESNPCLNG

GSCKDDINSYECWCPFGFEGKNCELDVTCNIKNGRCEQFCKNSADNKVVCSCTEGYRLAE

NQKSCEPAVPFPCGRVSVSQTSKLTRAETVFPDVDYVNSTEAETILDNITQSTQSFNDFTRV

VGGEDAKPGQFPWQVVLNGKVDAFCGGSIVNEKWIVTAAHCVETGVKITVVAGEHNIEETE

HTEQKRNVIRIIPHHNYNAAINKYNHDIALLELDEPLVLNSYVTPICIADKEYTNIFLKFGSGYV

SGWGRVFHKGRSALVLQYLRVPLVDRATCLLSTKFTIYNNMFCAGFHEGGRDSCQGDSGG

PHVTEVEGTSFLTGIISWGEECAMKGKYGIYTKVSRYVNWIKHKTKLT

>FIX variant R338W/E410H

SEQ ID NO: 13
YNSGKLEEFVQGNLERECMEEKCSFEEAREVFENTERTTEFWKQYVDGDQCESNPCLNG

GSCKDDINSYECWCPFGFEGKNCELDVTCNIKNGRCEQFCKNSADNKVVCSCTEGYRLAE

NQKSCEPAVPFPCGRVSVSQTSKLTRAETVFPDVDYVNSTEAETILDNITQSTQSFNDFTRV

-continued

VGGEDAKPGQFPWQVVLNGKVDAFCGGSIVNEKWIVTAAHCVETGVKITVVAGEHNIEETE

HTEQKRNVIRIIPHHNYNAAINKYNHDIALLELDEPLVLNSYVTPICIADKEYTNIFLKFGSGYV

SGWGRVFHKGRSALVLQYLRVPLVDRATCLWSTKFTIYNNMFCAGFHEGGRDSCQGDSG

GPHVTEVEGTSFLTGIISWGEECAMKGKYGIYTKVSRYVNWIKHKTKLT

>FIX variant R338L/E410H

SEQ ID NO: 14
YNSGKLEEFVQGNLERECMEEKCSFEEAREVFENTERTTEFWKQYVDGDQCESNPCLNG

GSCKDDINSYECWCPFGFEGKNCELDVTCNIKNGRCEQFCKNSADNKVVCSCTEGYRLAE

NQKSCEPAVPFPCGRVSVSQTSKLTRAETVFPDVDYVNSTEAETILDNITQSTQSFNDFTRV

VGGEDAKPGQFPWQVVLNGKVDAFCGGSIVNEKWIVTAAHCVETGVKITVVAGEHNIEETE

HTEQKRNVIRIIPHHNYNAAINKYNHDIALLELDEPLVLNSYVTPICIADKEYTNIFLKFGSGYV

SGWGRVFHKGRSALVLQYLRVPLVDRATCLLSTKFTIYNNMFCAGFHEGGRDSCQGDSGG

PHVTEVEGTSFLTGIISWGEECAMKGKYGIYTKVSRYVNWIKHKTKLT

>FIX variant R338V/E410H albumin fusion

SEQ ID NO: 15
YNSGKLEEFVQGNLERECMEEKCSFEEAREVFENTERTTEFWKQYVDGDQCESNPCLNG

GSCKDDINSYECWCPFGFEGKNCELDVTCNIKNGRCEQFCKNSADNKVVCSCTEGYRLAE

NQKSCEPAVPFPCGRVSVSQTSKLTRAETVFPDVDYVNSTEAETILDNITQSTQSFNDFTRV

VGGEDAKPGQFPWQVVLNGKVDAFCGGSIVNEKWIVTAAHCVETGVKITVVAGEHNIEETE

HTEQKRNVIRIIPHHNYNAAINKYNHDIALLELDEPLVLNSYVTPICIADKEYTNIFLKFGSGYV

SGWGRVFHKGRSALVLQYLRVPLVDRATCLVSTKFTIYNNMFCAGFHEGGRDSCQGDSGG

PHVTEVEGTSFLTGIISWGEECAMKGKYGIYTKVSRYVNWIKHKTKLTPVSQTSKLTRAETVF

PDVDAHKSEVAHRFKDLGEENFKALVLIAFAQYLQQCPFEDHVKLVNEVTEFAKTCVADESA

ENCDKSLHTLFGDKLCTVATLRETYGEMADCCAKQEPERNECFLQHKDDNPNLPRLVRPE

VDVMCTAFHDNEETFLKKYLYEIARRHPYFYAPELLFFAKRYKAAFTECCQAADKAACLLPK

LDELRDEGKASSAKQRLKCASLQKFGERAFKAWAVARLSQRFPKAEFAEVSKLVTDLTKVH

TECCHGDLLECADDRADLAKYICENQDSISSKLKECCEKPLLEKSHCIAEVENDEMPADLPS

LAADFVESKDVCKNYAEAKDVFLGMFLYEYARRHPDYSVVLLLRLAKTYETTLEKCCAAADP

HECYAKVFDEFKPLVEEPQNLIKQNCELFEQLGEYKFQNALLVRYTKKVPQVSTPTLVEVSR

NLGKVGSKCCKHPEAKRMPCAEDYLSVVLNQLCVLHEKTPVSDRVTKCCTESLVNRRPCF

SALEVDETYVPKEFNAETFTFHADICTLSEKERQIKKQTALVELVKHKPKATKEQLKAVMDDF

AAFVEKCCKADDKETCFAEEGKKLVAASQAALGL

>Human IgG1 Fc

SEQ ID NO: 16
EPKSCDKTHTCPPCPAPELLGGPSVFLFPPKPKDTLMISRTPEVTCVVVDVSHEDPEVKFN

WYVDGVEVHNAKTKPREEQYNSTYRVVSVLTVLHQDWLNGKEYKCKVSNKALPAPIEKTIS

KAKGQPREPQVYTLPPSRDELTKNQVSLTCLVKGFYPSDIAVEWESNGQPENNYKTTPPVL

DSDGSFFLYSKLTVDKSRWQQGNVFSCSVMHEALHNHYTQKSLSLSPG

>Human IgG1 Fc

SEQ ID NO: 17
DKTHTCPPCPAPELLGGPSVFLFPPKPKDTLMISRTPEVTCVVVDVSHEDPEVKFNWYVDG

VEVHNAKTKPREEQYNSTYRVVSVLTVLHQDWLNGKEYKCKVSNKALPAPIEKTISKAKGQ

PREPQVYTLPPSRDELTKNQVSLTCLVKGFYPSDIAVEWESNGQPENNYKTTPPVLDSDGS

FFLYSKLTVDKSRWQQGNVFSCSVMHEALHNHYTQKSLSLSPG

-continued

>CTP sequence

SEQ ID NO: 18

SSSSKAPPPS

>CTP sequence

SEQ ID NO: 19

DPRFQDSSSSKAPPPSLPSPSRLPGPSDTPIL

>CTP sequence

SEQ ID NO: 20

SSSSKAPPPSLPSPSRLPGPSDTPILPQ

>XTEN artificial sequence

SEQ ID NO: 21

GAPTSESATPESGPGSEPATSGSETPGTSESATPESGPGSEPATSGSETPGTSESATPES

GPGTSTEPSEGSAPGASS

>XTEN artificial sequence

SEQ ID NO: 22

GAPGSPAGSPTSTEEGTSESATPESGPGSEPATSGSETPASS

---

The invention claimed is:

1. A molecule comprising a Factor IX variant polypeptide of SEQ ID NOs: 11, 12, or 13.

2. The molecule of claim 1, wherein the molecule further comprises a half-life enhancing portion selected from the group consisting of: albumin, structurally related members of the albumin family, and fragments thereof; immunoglobulins without antigen binding domain; polyethylene glycol; CTP (C-terminal peptide of human chorionic gonadotropin) and fragments thereof; and an XTEN.

3. The molecule of claim 2, wherein the molecule further comprises a cleavable peptide linker between the Factor IX variant polypeptide and the half-life enhancing portion.

4. The molecule of claim 1, further comprising a linker of SEQ ID NO: 8, and a half-life enhancing portion of SEQ ID NO: 9.

5. The molecule of claim 1, wherein the Factor IX variant polypeptide is an activated version of the Factor IX variant polypeptide.

6. A nucleic acid encoding the molecule of claim 1.

7. A vector comprising the nucleic acid of claim 6.

8. A cell comprising the nucleic acid of claim 6.

9. A pharmaceutical composition comprising the molecule of claim 1 and a pharmaceutically acceptable carrier.

10. A pharmaceutical composition comprising the nucleic acid of claim 6 and a pharmaceutically acceptable carrier.

11. A pharmaceutical composition comprising the cell of claim 8 and a pharmaceutically acceptable carrier.

* * * * *

SEQUENCE LISTING

<160> NUMBER OF SEQ ID NOS: 23

<210> SEQ ID NO 1
<211> LENGTH: 415
<212> TYPE: PRT
<213> ORGANISM: Homo sapiens

<400> SEQUENCE: 1

```
Tyr Asn Ser Gly Lys Leu Glu Glu Phe Val Gln Gly Asn Leu Glu Arg
1               5                   10                  15

Glu Cys Met Glu Glu Lys Cys Ser Phe Glu Glu Ala Arg Glu Val Phe
            20                  25                  30

Glu Asn Thr Glu Arg Thr Thr Glu Phe Trp Lys Gln Tyr Val Asp Gly
        35                  40                  45

Asp Gln Cys Glu Ser Asn Pro Cys Leu Asn Gly Gly Ser Cys Lys Asp
    50                  55                  60

Asp Ile Asn Ser Tyr Glu Cys Trp Cys Pro Phe Gly Phe Glu Gly Lys
65                  70                  75                  80

Asn Cys Glu Leu Asp Val Thr Cys Asn Ile Lys Asn Gly Arg Cys Glu
            85                  90                  95

Gln Phe Cys Lys Asn Ser Ala Asp Asn Lys Val Val Cys Ser Cys Thr
            100                 105                 110

Glu Gly Tyr Arg Leu Ala Glu Asn Gln Lys Ser Cys Glu Pro Ala Val
        115                 120                 125

Pro Phe Pro Cys Gly Arg Val Ser Val Ser Gln Thr Ser Lys Leu Thr
    130                 135                 140

Arg Ala Glu Thr Val Phe Pro Asp Val Asp Tyr Val Asn Ser Thr Glu
145                 150                 155                 160

Ala Glu Thr Ile Leu Asp Asn Ile Thr Gln Ser Thr Gln Ser Phe Asn
                165                 170                 175

Asp Phe Thr Arg Val Val Gly Gly Glu Asp Ala Lys Pro Gly Gln Phe
                180                 185                 190

Pro Trp Gln Val Val Leu Asn Gly Lys Val Asp Ala Phe Cys Gly Gly
            195                 200                 205

Ser Ile Val Asn Glu Lys Trp Ile Val Thr Ala Ala His Cys Val Glu
    210                 215                 220

Thr Gly Val Lys Ile Thr Val Val Ala Gly Glu His Asn Ile Glu Glu
```

```
225                 230                 235                 240

Thr Glu His Thr Glu Gln Lys Arg Asn Val Ile Arg Ile Ile Pro His
                245                 250                 255

His Asn Tyr Asn Ala Ala Ile Asn Lys Tyr Asn His Asp Ile Ala Leu
                260                 265                 270

Leu Glu Leu Asp Glu Pro Leu Val Leu Asn Ser Tyr Val Thr Pro Ile
                275                 280                 285

Cys Ile Ala Asp Lys Glu Tyr Thr Asn Ile Phe Leu Lys Phe Gly Ser
                290                 295                 300

Gly Tyr Val Ser Gly Trp Gly Arg Val Phe His Lys Gly Arg Ser Ala
305                 310                 315                 320

Leu Val Leu Gln Tyr Leu Arg Val Pro Leu Val Asp Arg Ala Thr Cys
                325                 330                 335

Leu Arg Ser Thr Lys Phe Thr Ile Tyr Asn Asn Met Phe Cys Ala Gly
                340                 345                 350

Phe His Glu Gly Gly Arg Asp Ser Cys Gln Gly Asp Ser Gly Gly Pro
                355                 360                 365

His Val Thr Glu Val Glu Gly Thr Ser Phe Leu Thr Gly Ile Ile Ser
                370                 375                 380

Trp Gly Glu Glu Cys Ala Met Lys Gly Lys Tyr Gly Ile Tyr Thr Lys
385                 390                 395                 400

Val Ser Arg Tyr Val Asn Trp Ile Lys Glu Lys Thr Lys Leu Thr
                405                 410                 415
```

<210> SEQ ID NO 2
<211> LENGTH: 1251
<212> TYPE: DNA
<213> ORGANISM: Homo sapiens

<400> SEQUENCE: 2

```
atgtataatt caggtaaatt ggaagagttt gttcaaggga accttgagag agaatgtatg     60
gaagaaaagt gtagttttga agaagcacga gaagtttttg aaaacactga agaacaact    120 gaattttgga agcagtatgt tgatggagat cagtgtgagt ccaatccatg tttaaatggc    180
ggcagttgca aggatgacat taattcctat gaatgttggt gtccctttgg atttgaagga    240
aagaactgtg aattagatgt aacatgtaac attaagaatg gcagatgcga gcagttttgt    300
aaaaatagtg ctgataacaa ggtggtttgc tcctgtactg agggatatcg acttgcagaa    360
aaccagaagt cctgtgaacc agcagtgcca tttccatgtg gaagagtttc tgtttcacaa    420
acttctaagc tcacccgtgc tgagactgtt tttcctgatg tggactatgt aaattctact    480
gaagctgaaa ccattttgga taacatcact caaagcaccc aatcatttaa tgacttcact    540
cgggttgttg gtggagaaga tgccaaacca ggtcaattcc cttggcaggt tgttttgaat    600
ggtaaagttg atgcattctg tggaggctct atcgttaatg aaaaatggat tgtaactgct    660
gcccactgtg ttgaaactgg tgttaaaatt acagttgtcg caggtgaaca taatattgag    720
gagacagaac atacagagca aaagcgaaat gtgattcgaa ttattcctca ccacaactac    780
aatgcagcta ttaataagta caaccatgac attgcccttc tggaactgga cgaacccta    840 gtgctaaaca gctacgttac acctatttgc attgctgaca ggaatacac gaacatcttc    900 ctcaaatttg gatctggcta tgtaagtggc tggggaagag tcttccacaa agggagatca    960
gctttagttc ttcagtacct tagagttcca cttgttgacc gagccacatg tcttcgatct   1020
acaaagttca ccatctataa caacatgttc tgtgctggct ccatgaagg aggtagagat   1080
```

-continued

--- tcatgtcaag gagatagtgg gggacccat gttactgaag tggaagggac cagtttctta 1140
actggaatta ttagctgggg tgaagagtgt gcaatgaaag gcaaatatgg aatatatacc 1200
aaggtatccc ggtatgtcaa ctggattaag gaaaaaacaa agctcactta a 1251

<210> SEQ ID NO 3
<211> LENGTH: 461
<212> TYPE: PRT
<213> ORGANISM: Homo sapiens

<400> SEQUENCE: 3

Met Gln Arg Val Asn Met Ile Met Ala Glu Ser Pro Gly Leu Ile Thr
1               5                   10                  15

Ile Cys Leu Leu Gly Tyr Leu Leu Ser Ala Glu Cys Thr Val Phe Leu
                20                  25                  30

Asp His Glu Asn Ala Asn Lys Ile Leu Asn Arg Pro Lys Arg Tyr Asn
            35                  40                  45

Ser Gly Lys Leu Glu Glu Phe Val Gln Gly Asn Leu Glu Arg Glu Cys
        50                  55                  60

Met Glu Glu Lys Cys Ser Phe Glu Glu Ala Arg Glu Val Phe Glu Asn
65                  70                  75                  80

Thr Glu Arg Thr Thr Glu Phe Trp Lys Gln Tyr Val Asp Gly Asp Gln
                85                  90                  95

Cys Glu Ser Asn Pro Cys Leu Asn Gly Gly Ser Cys Lys Asp Asp Ile
            100                 105                 110

Asn Ser Tyr Glu Cys Trp Cys Pro Phe Gly Phe Glu Gly Lys Asn Cys
        115                 120                 125

Glu Leu Asp Val Thr Cys Asn Ile Lys Asn Gly Arg Cys Glu Gln Phe
    130                 135                 140

Cys Lys Asn Ser Ala Asp Asn Lys Val Val Cys Ser Cys Thr Glu Gly
145                 150                 155                 160

Tyr Arg Leu Ala Glu Asn Gln Lys Ser Cys Glu Pro Ala Val Pro Phe
                165                 170                 175

Pro Cys Gly Arg Val Ser Val Ser Gln Thr Ser Lys Leu Thr Arg Ala
            180                 185                 190

Glu Thr Val Phe Pro Asp Val Asp Tyr Val Asn Ser Thr Glu Ala Glu
        195                 200                 205

Thr Ile Leu Asp Asn Ile Thr Gln Ser Thr Gln Ser Phe Asn Asp Phe
    210                 215                 220

Thr Arg Val Val Gly Gly Glu Asp Ala Lys Pro Gly Gln Phe Pro Trp
225                 230                 235                 240

Gln Val Val Leu Asn Gly Lys Val Asp Ala Phe Cys Gly Gly Ser Ile
                245                 250                 255

Val Asn Glu Lys Trp Ile Val Thr Ala Ala His Cys Val Glu Thr Gly
            260                 265                 270

Val Lys Ile Thr Val Val Ala Gly Glu His Asn Ile Glu Glu Thr Glu
        275                 280                 285

His Thr Glu Gln Lys Arg Asn Val Ile Arg Ile Ile Pro His His Asn
    290                 295                 300

Tyr Asn Ala Ala Ile Asn Lys Tyr Asn His Asp Ile Ala Leu Leu Glu
305                 310                 315                 320

Leu Asp Glu Pro Leu Val Leu Asn Ser Tyr Val Thr Pro Ile Cys Ile
                325                 330                 335

Ala Asp Lys Glu Tyr Thr Asn Ile Phe Leu Lys Phe Gly Ser Gly Tyr
            340                 345                 350

```
Val Ser Gly Trp Gly Arg Val Phe His Lys Gly Arg Ser Ala Leu Val
        355                 360                 365

Leu Gln Tyr Leu Arg Val Pro Leu Val Asp Arg Ala Thr Cys Leu Arg
        370                 375                 380

Ser Thr Lys Phe Thr Ile Tyr Asn Asn Met Phe Cys Ala Gly Phe His
385                 390                 395                 400

Glu Gly Gly Arg Asp Ser Cys Gln Gly Asp Ser Gly Gly Pro His Val
                405                 410                 415

Thr Glu Val Glu Gly Thr Ser Phe Leu Thr Gly Ile Ile Ser Trp Gly
                420                 425                 430

Glu Glu Cys Ala Met Lys Gly Lys Tyr Gly Ile Tyr Thr Lys Val Ser
        435                 440                 445

Arg Tyr Val Asn Trp Ile Lys Glu Lys Thr Lys Leu Thr
        450                 455                 460

<210> SEQ ID NO 4
<211> LENGTH: 1386
<212> TYPE: DNA
<213> ORGANISM: Homo sapiens

<400> SEQUENCE: 4
atgcagcgcg tgaacatgat catggcagaa tcaccaggcc tcatcaccat ctgccttta      60 ggatatctac tcagtgctga atgtacagtt tttcttgatc atgaaacgc caacaaaatt      120 ctgaatcggc caaagaggta taattcaggt aaattggaag agtttgttca agggaacctt      180
gagagagaat gtatggaaga aaagtgtagt tttgaagaag cacgagaagt ttttgaaaac      240
actgaaagaa caactgaatt ttggaagcag tatgttgatg agatcagtg tgagtccaat      300 ccatgtttaa atggcggcag ttgcaaggat gacattaatt cctatgaatg ttggtgtccc      360
tttggatttg aaggaaagaa ctgtgaatta gatgtaacat gtaacattaa gaatggcaga      420
tgcgagcagt tttgtaaaaa tagtgctgat aacaaggtgg tttgctcctg tactgaggga      480
tatcgacttg cagaaaacca gaagtcctgt gaaccagcag tgccatttcc atgtggaaga      540
gtttctgttt cacaaacttc taagctcacc cgtgctgaga ctgtttttcc tgatgtggac      600
tatgtaaatt ctactgaagc tgaaaccatt ttggataaca tcactcaaag cacccaatca      660
tttaatgact tcactcgggt tgttggtgga aagatgcca aaccaggtca attcccttgg      720
caggttgttt tgaatggtaa agttgatgca ttctgtggag gctctatcgt taatgaaaaa      780
tggattgtaa ctgctgccca ctgtgttgaa actggtgtta aaattacagt tgtcgcaggt      840
gaacataata ttgaggagac agaacataca gagcaaaagc gaaatgtgat tcgaattatt      900
cctcaccaca actacaatgc agctattaat aagtacaacc atgacattgc ccttctggaa      960
ctggacgaac ccttagtgct aaacagctac gttacaccta tttgcattgc tgacaaggaa      1020
tacacgaaca tcttcctcaa atttggatct ggctatgtaa gtggctgggg aagagtcttc      1080
cacaaaggga gatcagcttt agttcttcag taccttagat ttccacttgt tgaccgagcc      1140
acatgtcttc gatctacaaa gttcaccatc tataacaaca tgttctgtgc tggcttccat      1200
gaaggaggta gagattcatg tcaaggagat agtgggggac cccatgttac tgaagtggaa      1260
gggaccagtt tcttaactgg aattattagc tggggtgaag agtgtgcaat gaaaggcaaa      1320
tatggaatat ataccaaggt atcccggtat gtcaactgga ttaaggaaaa aacaaagctc      1380
acttaa                                                                 1386
```

-continued

```
<210> SEQ ID NO 5
<211> LENGTH: 145
<212> TYPE: PRT
<213> ORGANISM: Homo sapiens

<400> SEQUENCE: 5

Tyr Asn Ser Gly Lys Leu Glu Glu Phe Val Gln Gly Asn Leu Glu Arg
1               5                   10                  15

Glu Cys Met Glu Glu Lys Cys Ser Phe Glu Glu Ala Arg Glu Val Phe
            20                  25                  30

Glu Asn Thr Glu Arg Thr Thr Glu Phe Trp Lys Gln Tyr Val Asp Gly
        35                  40                  45

Asp Gln Cys Glu Ser Asn Pro Cys Leu Asn Gly Gly Ser Cys Lys Asp
        50                  55                  60

Asp Ile Asn Ser Tyr Glu Cys Trp Cys Pro Phe Gly Phe Glu Gly Lys
65                  70                  75                  80

Asn Cys Glu Leu Asp Val Thr Cys Asn Ile Lys Asn Gly Arg Cys Glu
                85                  90                  95

Gln Phe Cys Lys Asn Ser Ala Asp Asn Lys Val Val Cys Ser Cys Thr
            100                 105                 110

Glu Gly Tyr Arg Leu Ala Glu Asn Gln Lys Ser Cys Glu Pro Ala Val
            115                 120                 125

Pro Phe Pro Cys Gly Arg Val Ser Val Ser Gln Thr Ser Lys Leu Thr
        130                 135                 140

Arg
145

<210> SEQ ID NO 6
<211> LENGTH: 235
<212> TYPE: PRT
<213> ORGANISM: Homo sapiens

<400> SEQUENCE: 6

Val Val Gly Gly Glu Asp Ala Lys Pro Gly Gln Phe Pro Trp Gln Val
1               5                   10                  15

Val Leu Asn Gly Lys Val Asp Ala Phe Cys Gly Gly Ser Ile Val Asn
            20                  25                  30

Glu Lys Trp Ile Val Thr Ala Ala His Cys Val Glu Thr Gly Val Lys
        35                  40                  45

Ile Thr Val Val Ala Gly Glu His Asn Ile Glu Glu Thr Glu His Thr
        50                  55                  60

Glu Gln Lys Arg Asn Val Ile Arg Ile Ile Pro His His Asn Tyr Asn
65                  70                  75                  80

Ala Ala Ile Asn Lys Tyr Asn His Asp Ile Ala Leu Leu Glu Leu Asp
                85                  90                  95

Glu Pro Leu Val Leu Asn Ser Tyr Val Thr Pro Ile Cys Ile Ala Asp
            100                 105                 110

Lys Glu Tyr Thr Asn Ile Phe Leu Lys Phe Gly Ser Gly Tyr Val Ser
            115                 120                 125

Gly Trp Gly Arg Val Phe His Lys Gly Arg Ser Ala Leu Val Leu Gln
        130                 135                 140

Tyr Leu Arg Val Pro Leu Val Asp Arg Ala Thr Cys Leu Arg Ser Thr
145                 150                 155                 160

Lys Phe Thr Ile Tyr Asn Asn Met Phe Cys Ala Gly Phe His Glu Gly
                165                 170                 175

Gly Arg Asp Ser Cys Gln Gly Asp Ser Gly Gly Pro His Val Thr Glu
```

-continued

```
                180             185             190

Val Glu Gly Thr Ser Phe Leu Thr Gly Ile Ile Ser Trp Gly Glu Glu
        195             200             205

Cys Ala Met Lys Gly Lys Tyr Gly Ile Tyr Thr Lys Val Ser Arg Tyr
    210             215             220

Val Asn Trp Ile Lys Glu Lys Thr Lys Leu Thr
225             230             235

<210> SEQ ID NO 7
<211> LENGTH: 415
<212> TYPE: PRT
<213> ORGANISM: Homo sapiens

<400> SEQUENCE: 7

Tyr Asn Ser Gly Lys Leu Glu Glu Phe Val Gln Gly Asn Leu Glu Arg
1               5               10              15

Glu Cys Met Glu Glu Lys Cys Ser Phe Glu Glu Ala Arg Glu Val Phe
            20              25              30

Glu Asn Thr Glu Arg Thr Thr Glu Phe Trp Lys Gln Tyr Val Asp Gly
        35              40              45

Asp Gln Cys Glu Ser Asn Pro Cys Leu Asn Gly Gly Ser Cys Lys Asp
    50              55              60

Asp Ile Asn Ser Tyr Glu Cys Trp Cys Pro Phe Gly Phe Glu Gly Lys
65              70              75              80

Asn Cys Glu Leu Asp Val Thr Cys Asn Ile Lys Asn Gly Arg Cys Glu
            85              90              95

Gln Phe Cys Lys Asn Ser Ala Asp Asn Lys Val Val Cys Ser Cys Thr
            100             105             110

Glu Gly Tyr Arg Leu Ala Glu Asn Gln Lys Ser Cys Glu Pro Ala Val
            115             120             125

Pro Phe Pro Cys Gly Arg Val Ser Val Ser Gln Thr Ser Lys Leu Thr
    130             135             140

Arg Ala Glu Ala Val Phe Pro Asp Val Asp Tyr Val Asn Ser Thr Glu
145             150             155             160

Ala Glu Thr Ile Leu Asp Asn Ile Thr Gln Ser Thr Gln Ser Phe Asn
            165             170             175

Asp Phe Thr Arg Val Val Gly Gly Glu Asp Ala Lys Pro Gly Gln Phe
            180             185             190

Pro Trp Gln Val Val Leu Asn Gly Lys Val Asp Ala Phe Cys Gly Gly
        195             200             205

Ser Ile Val Asn Glu Lys Trp Ile Val Thr Ala Ala His Cys Val Glu
    210             215             220

Thr Gly Val Lys Ile Thr Val Val Ala Gly Glu His Asn Ile Glu Glu
225             230             235             240

Thr Glu His Thr Glu Gln Lys Arg Asn Val Ile Arg Ile Ile Pro His
            245             250             255

His Asn Tyr Asn Ala Ala Ile Asn Lys Tyr Asn His Asp Ile Ala Leu
            260             265             270

Leu Glu Leu Asp Glu Pro Leu Val Leu Asn Ser Tyr Val Thr Pro Ile
        275             280             285

Cys Ile Ala Asp Lys Glu Tyr Thr Asn Ile Phe Leu Lys Phe Gly Ser
    290             295             300

Gly Tyr Val Ser Gly Trp Gly Arg Val Phe His Lys Gly Arg Ser Ala
305             310             315             320
```

```
Leu Val Leu Gln Tyr Leu Arg Val Pro Leu Val Asp Arg Ala Thr Cys
            325                 330                 335

Leu Arg Ser Thr Lys Phe Thr Ile Tyr Asn Asn Met Phe Cys Ala Gly
            340                 345                 350

Phe His Glu Gly Gly Arg Asp Ser Cys Gln Gly Asp Ser Gly Gly Pro
            355                 360                 365

His Val Thr Glu Val Glu Gly Thr Ser Phe Leu Thr Gly Ile Ile Ser
        370                 375                 380

Trp Gly Glu Glu Cys Ala Met Lys Gly Lys Tyr Gly Ile Tyr Thr Lys
385                 390                 395                 400

Val Ser Arg Tyr Val Asn Trp Ile Lys Glu Lys Thr Lys Leu Thr
                405                 410                 415

<210> SEQ ID NO 8
<211> LENGTH: 18
<212> TYPE: PRT
<213> ORGANISM: Artificial Sequence
<220> FEATURE:
<223> OTHER INFORMATION: Linker

<400> SEQUENCE: 8

Pro Val Ser Gln Thr Ser Lys Leu Thr Arg Ala Glu Thr Val Phe Pro
1               5                   10                  15

Asp Val

<210> SEQ ID NO 9
<211> LENGTH: 585
<212> TYPE: PRT
<213> ORGANISM: Homo sapiens

<400> SEQUENCE: 9

Asp Ala His Lys Ser Glu Val Ala His Arg Phe Lys Asp Leu Gly Glu
1               5                   10                  15

Glu Asn Phe Lys Ala Leu Val Leu Ile Ala Phe Ala Gln Tyr Leu Gln
            20                  25                  30

Gln Cys Pro Phe Glu Asp His Val Lys Leu Val Asn Glu Val Thr Glu
            35                  40                  45

Phe Ala Lys Thr Cys Val Ala Asp Glu Ser Ala Glu Asn Cys Asp Lys
        50                  55                  60

Ser Leu His Thr Leu Phe Gly Asp Lys Leu Cys Thr Val Ala Thr Leu
65                  70                  75                  80

Arg Glu Thr Tyr Gly Glu Met Ala Asp Cys Cys Ala Lys Gln Glu Pro
                85                  90                  95

Glu Arg Asn Glu Cys Phe Leu Gln His Lys Asp Asp Asn Pro Asn Leu
            100                 105                 110

Pro Arg Leu Val Arg Pro Glu Val Asp Val Met Cys Thr Ala Phe His
            115                 120                 125

Asp Asn Glu Glu Thr Phe Leu Lys Lys Tyr Leu Tyr Glu Ile Ala Arg
        130                 135                 140

Arg His Pro Tyr Phe Tyr Ala Pro Glu Leu Leu Phe Phe Ala Lys Arg
145                 150                 155                 160

Tyr Lys Ala Ala Phe Thr Glu Cys Cys Gln Ala Ala Asp Lys Ala Ala
                165                 170                 175

Cys Leu Leu Pro Lys Leu Asp Glu Leu Arg Asp Glu Gly Lys Ala Ser
            180                 185                 190

Ser Ala Lys Gln Arg Leu Lys Cys Ala Ser Leu Gln Lys Phe Gly Glu
            195                 200                 205
```

-continued

```
Arg Ala Phe Lys Ala Trp Ala Val Ala Arg Leu Ser Gln Arg Phe Pro
    210             215             220

Lys Ala Glu Phe Ala Glu Val Ser Lys Leu Val Thr Asp Leu Thr Lys
225             230             235             240

Val His Thr Glu Cys Cys His Gly Asp Leu Leu Glu Cys Ala Asp Asp
                245             250             255

Arg Ala Asp Leu Ala Lys Tyr Ile Cys Glu Asn Gln Asp Ser Ile Ser
            260             265             270

Ser Lys Leu Lys Glu Cys Cys Glu Lys Pro Leu Leu Glu Lys Ser His
        275             280             285

Cys Ile Ala Glu Val Glu Asn Asp Glu Met Pro Ala Asp Leu Pro Ser
    290             295             300

Leu Ala Ala Asp Phe Val Glu Ser Lys Asp Val Cys Lys Asn Tyr Ala
305             310             315             320

Glu Ala Lys Asp Val Phe Leu Gly Met Phe Leu Tyr Glu Tyr Ala Arg
            325             330             335

Arg His Pro Asp Tyr Ser Val Val Leu Leu Leu Arg Leu Ala Lys Thr
            340             345             350

Tyr Glu Thr Thr Leu Glu Lys Cys Cys Ala Ala Ala Asp Pro His Glu
        355             360             365

Cys Tyr Ala Lys Val Phe Asp Glu Phe Lys Pro Leu Val Glu Glu Pro
    370             375             380

Gln Asn Leu Ile Lys Gln Asn Cys Glu Leu Phe Glu Gln Leu Gly Glu
385             390             395             400

Tyr Lys Phe Gln Asn Ala Leu Leu Val Arg Tyr Thr Lys Lys Val Pro
            405             410             415

Gln Val Ser Thr Pro Thr Leu Val Glu Val Ser Arg Asn Leu Gly Lys
            420             425             430

Val Gly Ser Lys Cys Cys Lys His Pro Glu Ala Lys Arg Met Pro Cys
        435             440             445

Ala Glu Asp Tyr Leu Ser Val Val Leu Asn Gln Leu Cys Val Leu His
    450             455             460

Glu Lys Thr Pro Val Ser Asp Arg Val Thr Lys Cys Cys Thr Glu Ser
465             470             475             480

Leu Val Asn Arg Arg Pro Cys Phe Ser Ala Leu Glu Val Asp Glu Thr
            485             490             495

Tyr Val Pro Lys Glu Phe Asn Ala Glu Thr Phe Thr Phe His Ala Asp
            500             505             510

Ile Cys Thr Leu Ser Glu Lys Glu Arg Gln Ile Lys Lys Gln Thr Ala
        515             520             525

Leu Val Glu Leu Val Lys His Lys Pro Lys Ala Thr Lys Glu Gln Leu
    530             535             540

Lys Ala Val Met Asp Asp Phe Ala Ala Phe Val Glu Lys Cys Cys Lys
545             550             555             560

Ala Asp Asp Lys Glu Thr Cys Phe Ala Glu Glu Gly Lys Lys Leu Val
            565             570             575

Ala Ala Ser Gln Ala Ala Leu Gly Leu
            580             585
```

<210> SEQ ID NO 10
<211> LENGTH: 1018
<212> TYPE: PRT
<213> ORGANISM: Artificial Sequence
<220> FEATURE:

```
<223> OTHER INFORMATION: FIX (wild-type) albumin fusion protein

<400> SEQUENCE: 10

Tyr Asn Ser Gly Lys Leu Glu Glu Phe Val Gln Gly Asn Leu Glu Arg
1               5                   10                  15

Glu Cys Met Glu Glu Lys Cys Ser Phe Glu Glu Ala Arg Glu Val Phe
            20                  25                  30

Glu Asn Thr Glu Arg Thr Thr Glu Phe Trp Lys Gln Tyr Val Asp Gly
        35                  40                  45

Asp Gln Cys Glu Ser Asn Pro Cys Leu Asn Gly Gly Ser Cys Lys Asp
    50                  55                  60

Asp Ile Asn Ser Tyr Glu Cys Trp Cys Pro Phe Gly Phe Glu Gly Lys
65                  70                  75                  80

Asn Cys Glu Leu Asp Val Thr Cys Asn Ile Lys Asn Gly Arg Cys Glu
                85                  90                  95

Gln Phe Cys Lys Asn Ser Ala Asp Asn Lys Val Val Cys Ser Cys Thr
            100                 105                 110

Glu Gly Tyr Arg Leu Ala Glu Asn Gln Lys Ser Cys Glu Pro Ala Val
        115                 120                 125

Pro Phe Pro Cys Gly Arg Val Ser Val Ser Gln Thr Ser Lys Leu Thr
    130                 135                 140

Arg Ala Glu Thr Val Phe Pro Asp Val Asp Tyr Val Asn Ser Thr Glu
145                 150                 155                 160

Ala Glu Thr Ile Leu Asp Asn Ile Thr Gln Ser Thr Gln Ser Phe Asn
                165                 170                 175

Asp Phe Thr Arg Val Val Gly Gly Glu Asp Ala Lys Pro Gly Gln Phe
            180                 185                 190

Pro Trp Gln Val Val Leu Asn Gly Lys Val Asp Ala Phe Cys Gly Gly
        195                 200                 205

Ser Ile Val Asn Glu Lys Trp Ile Val Thr Ala Ala His Cys Val Glu
    210                 215                 220

Thr Gly Val Lys Ile Thr Val Val Ala Gly Glu His Asn Ile Glu Glu
225                 230                 235                 240

Thr Glu His Thr Glu Gln Lys Arg Asn Val Ile Arg Ile Ile Pro His
                245                 250                 255

His Asn Tyr Asn Ala Ala Ile Asn Lys Tyr Asn His Asp Ile Ala Leu
            260                 265                 270

Leu Glu Leu Asp Glu Pro Leu Val Leu Asn Ser Tyr Val Thr Pro Ile
        275                 280                 285

Cys Ile Ala Asp Lys Glu Tyr Thr Asn Ile Phe Leu Lys Phe Gly Ser
    290                 295                 300

Gly Tyr Val Ser Gly Trp Gly Arg Val Phe His Lys Gly Arg Ser Ala
305                 310                 315                 320

Leu Val Leu Gln Tyr Leu Arg Val Pro Leu Val Asp Arg Ala Thr Cys
                325                 330                 335

Leu Arg Ser Thr Lys Phe Thr Ile Tyr Asn Asn Met Phe Cys Ala Gly
            340                 345                 350

Phe His Glu Gly Gly Arg Asp Ser Cys Gln Gly Asp Ser Gly Gly Pro
        355                 360                 365

His Val Thr Glu Val Glu Gly Thr Ser Phe Leu Thr Gly Ile Ile Ser
    370                 375                 380

Trp Gly Glu Glu Cys Ala Met Lys Gly Lys Tyr Gly Ile Tyr Thr Lys
385                 390                 395                 400
```

-continued

```
Val Ser Arg Tyr Val Asn Trp Ile Lys Glu Lys Thr Lys Leu Thr Pro
            405             410             415

Val Ser Gln Thr Ser Lys Leu Thr Arg Ala Glu Thr Val Phe Pro Asp
            420             425             430

Val Asp Ala His Lys Ser Glu Val Ala His Arg Phe Lys Asp Leu Gly
        435             440             445

Glu Glu Asn Phe Lys Ala Leu Val Leu Ile Ala Phe Ala Gln Tyr Leu
    450             455             460

Gln Gln Cys Pro Phe Glu Asp His Val Lys Leu Val Asn Glu Val Thr
465             470             475             480

Glu Phe Ala Lys Thr Cys Val Ala Asp Glu Ser Ala Glu Asn Cys Asp
            485             490             495

Lys Ser Leu His Thr Leu Phe Gly Asp Lys Leu Cys Thr Val Ala Thr
            500             505             510

Leu Arg Glu Thr Tyr Gly Glu Met Ala Asp Cys Cys Ala Lys Gln Glu
            515             520             525

Pro Glu Arg Asn Glu Cys Phe Leu Gln His Lys Asp Asp Asn Pro Asn
            530             535             540

Leu Pro Arg Leu Val Arg Pro Glu Val Asp Val Met Cys Thr Ala Phe
545             550             555             560

His Asp Asn Glu Glu Thr Phe Leu Lys Lys Tyr Leu Tyr Glu Ile Ala
            565             570             575

Arg Arg His Pro Tyr Phe Tyr Ala Pro Glu Leu Leu Phe Phe Ala Lys
            580             585             590

Arg Tyr Lys Ala Ala Phe Thr Glu Cys Cys Gln Ala Ala Asp Lys Ala
            595             600             605

Ala Cys Leu Leu Pro Lys Leu Asp Glu Leu Arg Asp Glu Gly Lys Ala
        610             615             620

Ser Ser Ala Lys Gln Arg Leu Lys Cys Ala Ser Leu Gln Lys Phe Gly
625             630             635             640

Glu Arg Ala Phe Lys Ala Trp Ala Val Ala Arg Leu Ser Gln Arg Phe
            645             650             655

Pro Lys Ala Glu Phe Ala Glu Val Ser Lys Leu Val Thr Asp Leu Thr
            660             665             670

Lys Val His Thr Glu Cys Cys His Gly Asp Leu Leu Glu Cys Ala Asp
            675             680             685

Asp Arg Ala Asp Leu Ala Lys Tyr Ile Cys Glu Asn Gln Asp Ser Ile
        690             695             700

Ser Ser Lys Leu Lys Glu Cys Cys Glu Lys Pro Leu Leu Glu Lys Ser
705             710             715             720

His Cys Ile Ala Glu Val Glu Asn Asp Glu Met Pro Ala Asp Leu Pro
            725             730             735

Ser Leu Ala Ala Asp Phe Val Glu Ser Lys Asp Val Cys Lys Asn Tyr
            740             745             750

Ala Glu Ala Lys Asp Val Phe Leu Gly Met Phe Leu Tyr Glu Tyr Ala
            755             760             765

Arg Arg His Pro Asp Tyr Ser Val Val Leu Leu Leu Arg Leu Ala Lys
            770             775             780

Thr Tyr Glu Thr Thr Leu Glu Lys Cys Cys Ala Ala Ala Asp Pro His
785             790             795             800

Glu Cys Tyr Ala Lys Val Phe Asp Glu Phe Lys Pro Leu Val Glu Glu
            805             810             815

Pro Gln Asn Leu Ile Lys Gln Asn Cys Glu Leu Phe Glu Gln Leu Gly
```

-continued

```
                 820                    825                    830
Glu Tyr Lys Phe Gln Asn Ala Leu Leu Val Arg Tyr Thr Lys Lys Val
            835                    840                    845
Pro Gln Val Ser Thr Pro Thr Leu Val Glu Val Ser Arg Asn Leu Gly
        850                    855                    860
Lys Val Gly Ser Lys Cys Cys Lys His Pro Glu Ala Lys Arg Met Pro
865                    870                    875                    880
Cys Ala Glu Asp Tyr Leu Ser Val Val Leu Asn Gln Leu Cys Val Leu
                885                    890                    895
His Glu Lys Thr Pro Val Ser Asp Arg Val Thr Lys Cys Cys Thr Glu
            900                    905                    910
Ser Leu Val Asn Arg Arg Pro Cys Phe Ser Ala Leu Glu Val Asp Glu
            915                    920                    925
Thr Tyr Val Pro Lys Glu Phe Asn Ala Glu Thr Phe Thr Phe His Ala
        930                    935                    940
Asp Ile Cys Thr Leu Ser Glu Lys Glu Arg Gln Ile Lys Lys Gln Thr
945                    950                    955                    960
Ala Leu Val Glu Leu Val Lys His Lys Pro Lys Ala Thr Lys Glu Gln
                965                    970                    975
Leu Lys Ala Val Met Asp Asp Phe Ala Ala Phe Val Glu Lys Cys Cys
                980                    985                    990
Lys Ala Asp Asp Lys Glu Thr Cys Phe Ala Glu Glu Gly Lys Lys Leu
            995                    1000                   1005
Val Ala Ala Ser Gln Ala Ala Leu Gly Leu
        1010                   1015
```

<210> SEQ ID NO 11
<211> LENGTH: 415
<212> TYPE: PRT
<213> ORGANISM: Artificial Sequence
<220> FEATURE:
<223> OTHER INFORMATION: FIX variant R338V/E410H

<400> SEQUENCE: 11

```
Tyr Asn Ser Gly Lys Leu Glu Glu Phe Val Gln Gly Asn Leu Glu Arg
1                   5                    10                     15
Glu Cys Met Glu Glu Lys Cys Ser Phe Glu Glu Ala Arg Glu Val Phe
                20                    25                     30
Glu Asn Thr Glu Arg Thr Thr Glu Phe Trp Lys Gln Tyr Val Asp Gly
            35                    40                     45
Asp Gln Cys Glu Ser Asn Pro Cys Leu Asn Gly Gly Ser Cys Lys Asp
        50                    55                     60
Asp Ile Asn Ser Tyr Glu Cys Trp Cys Pro Phe Gly Phe Glu Gly Lys
65                    70                    75                     80
Asn Cys Glu Leu Asp Val Thr Cys Asn Ile Lys Asn Gly Arg Cys Glu
                85                    90                     95
Gln Phe Cys Lys Asn Ser Ala Asp Asn Lys Val Val Cys Ser Cys Thr
                100                   105                    110
Glu Gly Tyr Arg Leu Ala Glu Asn Gln Lys Ser Cys Glu Pro Ala Val
            115                   120                    125
Pro Phe Pro Cys Gly Arg Val Ser Val Ser Gln Thr Ser Lys Leu Thr
        130                   135                    140
Arg Ala Glu Thr Val Phe Pro Asp Val Asp Tyr Val Asn Ser Thr Glu
145                   150                   155                    160
Ala Glu Thr Ile Leu Asp Asn Ile Thr Gln Ser Thr Gln Ser Phe Asn
```

```
              165              170              175

Asp Phe Thr Arg Val Val Gly Gly Glu Asp Ala Lys Pro Gly Gln Phe
            180              185              190

Pro Trp Gln Val Val Leu Asn Gly Lys Val Asp Ala Phe Cys Gly Gly
        195              200              205

Ser Ile Val Asn Glu Lys Trp Ile Val Thr Ala Ala His Cys Val Glu
        210              215              220

Thr Gly Val Lys Ile Thr Val Val Ala Gly Glu His Asn Ile Glu Glu
225              230              235              240

Thr Glu His Thr Glu Gln Lys Arg Asn Val Ile Arg Ile Ile Pro His
            245              250              255

His Asn Tyr Asn Ala Ala Ile Asn Lys Tyr Asn His Asp Ile Ala Leu
            260              265              270

Leu Glu Leu Asp Glu Pro Leu Val Leu Asn Ser Tyr Val Thr Pro Ile
        275              280              285

Cys Ile Ala Asp Lys Glu Tyr Thr Asn Ile Phe Leu Lys Phe Gly Ser
        290              295              300

Gly Tyr Val Ser Gly Trp Gly Arg Val Phe His Lys Gly Arg Ser Ala
305              310              315              320

Leu Val Leu Gln Tyr Leu Arg Val Pro Leu Val Asp Arg Ala Thr Cys
            325              330              335

Leu Val Ser Thr Lys Phe Thr Ile Tyr Asn Asn Met Phe Cys Ala Gly
            340              345              350

Phe His Glu Gly Gly Arg Asp Ser Cys Gln Gly Asp Ser Gly Gly Pro
            355              360              365

His Val Thr Glu Val Glu Gly Thr Ser Phe Leu Thr Gly Ile Ile Ser
        370              375              380

Trp Gly Glu Glu Cys Ala Met Lys Gly Lys Tyr Gly Ile Tyr Thr Lys
385              390              395              400

Val Ser Arg Tyr Val Asn Trp Ile Lys His Lys Thr Lys Leu Thr
            405              410              415
```

<210> SEQ ID NO 12
<211> LENGTH: 415
<212> TYPE: PRT
<213> ORGANISM: Artificial Sequence
<220> FEATURE:
<223> OTHER INFORMATION: FIX variant R338T/E410H

<400> SEQUENCE: 12

```
Tyr Asn Ser Gly Lys Leu Glu Glu Phe Val Gln Gly Asn Leu Glu Arg
1               5               10              15

Glu Cys Met Glu Glu Lys Cys Ser Phe Glu Glu Ala Arg Glu Val Phe
            20              25              30

Glu Asn Thr Glu Arg Thr Thr Glu Phe Trp Lys Gln Tyr Val Asp Gly
        35              40              45

Asp Gln Cys Glu Ser Asn Pro Cys Leu Asn Gly Gly Ser Cys Lys Asp
        50              55              60

Asp Ile Asn Ser Tyr Glu Cys Trp Cys Pro Phe Gly Phe Glu Gly Lys
65              70              75              80

Asn Cys Glu Leu Asp Val Thr Cys Asn Ile Lys Asn Gly Arg Cys Glu
            85              90              95

Gln Phe Cys Lys Asn Ser Ala Asp Asn Lys Val Val Cys Ser Cys Thr
            100             105             110

Glu Gly Tyr Arg Leu Ala Glu Asn Gln Lys Ser Cys Glu Pro Ala Val
```

```
            115                 120                 125
Pro Phe Pro Cys Gly Arg Val Ser Val Ser Gln Thr Ser Lys Leu Thr
    130                 135                 140

Arg Ala Glu Thr Val Phe Pro Asp Val Asp Tyr Val Asn Ser Thr Glu
145                 150                 155                 160

Ala Glu Thr Ile Leu Asp Asn Ile Thr Gln Ser Thr Gln Ser Phe Asn
                165                 170                 175

Asp Phe Thr Arg Val Val Gly Gly Glu Asp Ala Lys Pro Gly Gln Phe
                180                 185                 190

Pro Trp Gln Val Val Leu Asn Gly Lys Val Asp Ala Phe Cys Gly Gly
                195                 200                 205

Ser Ile Val Asn Glu Lys Trp Ile Val Thr Ala Ala His Cys Val Glu
    210                 215                 220

Thr Gly Val Lys Ile Thr Val Val Ala Gly Glu His Asn Ile Glu Glu
225                 230                 235                 240

Thr Glu His Thr Glu Gln Lys Arg Asn Val Ile Arg Ile Ile Pro His
                245                 250                 255

His Asn Tyr Asn Ala Ala Ile Asn Lys Tyr Asn His Asp Ile Ala Leu
                260                 265                 270

Leu Glu Leu Asp Glu Pro Leu Val Leu Asn Ser Tyr Val Thr Pro Ile
                275                 280                 285

Cys Ile Ala Asp Lys Glu Tyr Thr Asn Ile Phe Leu Lys Phe Gly Ser
    290                 295                 300

Gly Tyr Val Ser Gly Trp Gly Arg Val Phe His Lys Gly Arg Ser Ala
305                 310                 315                 320

Leu Val Leu Gln Tyr Leu Arg Val Pro Leu Val Asp Arg Ala Thr Cys
                325                 330                 335

Leu Thr Ser Thr Lys Phe Thr Ile Tyr Asn Asn Met Phe Cys Ala Gly
                340                 345                 350

Phe His Glu Gly Gly Arg Asp Ser Cys Gln Gly Asp Ser Gly Gly Pro
                355                 360                 365

His Val Thr Glu Val Glu Gly Thr Ser Phe Leu Thr Gly Ile Ile Ser
    370                 375                 380

Trp Gly Glu Glu Cys Ala Met Lys Gly Lys Tyr Gly Ile Tyr Thr Lys
385                 390                 395                 400

Val Ser Arg Tyr Val Asn Trp Ile Lys His Lys Thr Lys Leu Thr
                405                 410                 415
```

<210> SEQ ID NO 13
<211> LENGTH: 415
<212> TYPE: PRT
<213> ORGANISM: Artificial Sequence
<220> FEATURE:
<223> OTHER INFORMATION: FIX variant R338W/E410H

<400> SEQUENCE: 13

```
Tyr Asn Ser Gly Lys Leu Glu Glu Phe Val Gln Gly Asn Leu Glu Arg
1               5                   10                  15

Glu Cys Met Glu Glu Lys Cys Ser Phe Glu Glu Ala Arg Glu Val Phe
                20                  25                  30

Glu Asn Thr Glu Arg Thr Thr Glu Phe Trp Lys Gln Tyr Val Asp Gly
                35                  40                  45

Asp Gln Cys Glu Ser Asn Pro Cys Leu Asn Gly Gly Ser Cys Lys Asp
    50                  55                  60

Asp Ile Asn Ser Tyr Glu Cys Trp Cys Pro Phe Gly Phe Glu Gly Lys
```

```
65                    70                    75                    80

Asn Cys Glu Leu Asp Val Thr Cys Asn Ile Lys Asn Gly Arg Cys Glu
                85                    90                    95

Gln Phe Cys Lys Asn Ser Ala Asp Asn Lys Val Val Cys Ser Cys Thr
                100                   105                   110

Glu Gly Tyr Arg Leu Ala Glu Asn Gln Lys Ser Cys Glu Pro Ala Val
                115                   120                   125

Pro Phe Pro Cys Gly Arg Val Ser Val Ser Gln Thr Ser Lys Leu Thr
        130                   135                   140

Arg Ala Glu Thr Val Phe Pro Asp Val Asp Tyr Val Asn Ser Thr Glu
145                   150                   155                   160

Ala Glu Thr Ile Leu Asp Asn Ile Thr Gln Ser Thr Gln Ser Phe Asn
                165                   170                   175

Asp Phe Thr Arg Val Val Gly Gly Glu Asp Ala Lys Pro Gly Gln Phe
                180                   185                   190

Pro Trp Gln Val Val Leu Asn Gly Lys Val Asp Ala Phe Cys Gly Gly
                195                   200                   205

Ser Ile Val Asn Glu Lys Trp Ile Val Thr Ala Ala His Cys Val Glu
        210                   215                   220

Thr Gly Val Lys Ile Thr Val Val Ala Gly Glu His Asn Ile Glu Glu
225                   230                   235                   240

Thr Glu His Thr Glu Gln Lys Arg Asn Val Ile Arg Ile Ile Pro His
                245                   250                   255

His Asn Tyr Asn Ala Ala Ile Asn Lys Tyr Asn His Asp Ile Ala Leu
                260                   265                   270

Leu Glu Leu Asp Glu Pro Leu Val Leu Asn Ser Tyr Val Thr Pro Ile
                275                   280                   285

Cys Ile Ala Asp Lys Glu Tyr Thr Asn Ile Phe Leu Lys Phe Gly Ser
        290                   295                   300

Gly Tyr Val Ser Gly Trp Gly Arg Val Phe His Lys Gly Arg Ser Ala
305                   310                   315                   320

Leu Val Leu Gln Tyr Leu Arg Val Pro Leu Val Asp Arg Ala Thr Cys
                325                   330                   335

Leu Trp Ser Thr Lys Phe Thr Ile Tyr Asn Asn Met Phe Cys Ala Gly
                340                   345                   350

Phe His Glu Gly Gly Arg Asp Ser Cys Gln Gly Asp Ser Gly Gly Pro
                355                   360                   365

His Val Thr Glu Val Glu Gly Thr Ser Phe Leu Thr Gly Ile Ile Ser
        370                   375                   380

Trp Gly Glu Glu Cys Ala Met Lys Gly Lys Tyr Gly Ile Tyr Thr Lys
385                   390                   395                   400

Val Ser Arg Tyr Val Asn Trp Ile Lys His Lys Thr Lys Leu Thr
                405                   410                   415

<210> SEQ ID NO 14
<211> LENGTH: 415
<212> TYPE: PRT
<213> ORGANISM: Artificial Sequence
<220> FEATURE:
<223> OTHER INFORMATION: FIX variant R338L/E410H

<400> SEQUENCE: 14

Tyr Asn Ser Gly Lys Leu Glu Glu Phe Val Gln Gly Asn Leu Glu Arg
1               5                   10                  15

Glu Cys Met Glu Glu Lys Cys Ser Phe Glu Glu Ala Arg Glu Val Phe
```

-continued

```
              20                25                30

Glu Asn Thr Glu Arg Thr Thr Glu Phe Trp Lys Gln Tyr Val Asp Gly
          35                40                45

Asp Gln Cys Glu Ser Asn Pro Cys Leu Asn Gly Gly Ser Cys Lys Asp
      50                55                60

Asp Ile Asn Ser Tyr Glu Cys Trp Cys Pro Phe Gly Phe Glu Gly Lys
65                70                75                80

Asn Cys Glu Leu Asp Val Thr Cys Asn Ile Lys Asn Gly Arg Cys Glu
              85                90                95

Gln Phe Cys Lys Asn Ser Ala Asp Asn Lys Val Val Cys Ser Cys Thr
          100               105               110

Glu Gly Tyr Arg Leu Ala Glu Asn Gln Lys Ser Cys Glu Pro Ala Val
              115               120               125

Pro Phe Pro Cys Gly Arg Val Ser Val Ser Gln Thr Ser Lys Leu Thr
          130               135               140

Arg Ala Glu Thr Val Phe Pro Asp Val Asp Tyr Val Asn Ser Thr Glu
145               150               155               160

Ala Glu Thr Ile Leu Asp Asn Ile Thr Gln Ser Thr Gln Ser Phe Asn
              165               170               175

Asp Phe Thr Arg Val Val Gly Gly Glu Asp Ala Lys Pro Gly Gln Phe
              180               185               190

Pro Trp Gln Val Val Leu Asn Gly Lys Val Asp Ala Phe Cys Gly Gly
          195               200               205

Ser Ile Val Asn Glu Lys Trp Ile Val Thr Ala Ala His Cys Val Glu
      210               215               220

Thr Gly Val Lys Ile Thr Val Val Ala Gly Glu His Asn Ile Glu Glu
225               230               235               240

Thr Glu His Thr Glu Gln Lys Arg Asn Val Ile Arg Ile Ile Pro His
              245               250               255

His Asn Tyr Asn Ala Ala Ile Asn Lys Tyr Asn His Asp Ile Ala Leu
              260               265               270

Leu Glu Leu Asp Glu Pro Leu Val Leu Asn Ser Tyr Val Thr Pro Ile
          275               280               285

Cys Ile Ala Asp Lys Glu Tyr Thr Asn Ile Phe Leu Lys Phe Gly Ser
      290               295               300

Gly Tyr Val Ser Gly Trp Gly Arg Val Phe His Lys Gly Arg Ser Ala
305               310               315               320

Leu Val Leu Gln Tyr Leu Arg Val Pro Leu Val Asp Arg Ala Thr Cys
              325               330               335

Leu Leu Ser Thr Lys Phe Thr Ile Tyr Asn Asn Met Phe Cys Ala Gly
              340               345               350

Phe His Glu Gly Gly Arg Asp Ser Cys Gln Gly Asp Ser Gly Gly Pro
          355               360               365

His Val Thr Glu Val Glu Gly Thr Ser Phe Leu Thr Gly Ile Ile Ser
      370               375               380

Trp Gly Glu Glu Cys Ala Met Lys Gly Lys Tyr Gly Ile Tyr Thr Lys
385               390               395               400

Val Ser Arg Tyr Val Asn Trp Ile Lys His Lys Thr Lys Leu Thr
              405               410               415
```

<210> SEQ ID NO 15
<211> LENGTH: 1018
<212> TYPE: PRT
<213> ORGANISM: Artificial Sequence -continued

```
<220> FEATURE:
<223> OTHER INFORMATION: FIX variant R338V/E410H albumin fusion

<400> SEQUENCE: 15

Tyr Asn Ser Gly Lys Leu Glu Glu Phe Val Gln Gly Asn Leu Glu Arg
1               5                   10                  15

Glu Cys Met Glu Glu Lys Cys Ser Phe Glu Glu Ala Arg Glu Val Phe
            20                  25                  30

Glu Asn Thr Glu Arg Thr Thr Glu Phe Trp Lys Gln Tyr Val Asp Gly
        35                  40                  45

Asp Gln Cys Glu Ser Asn Pro Cys Leu Asn Gly Gly Ser Cys Lys Asp
    50                  55                  60

Asp Ile Asn Ser Tyr Glu Cys Trp Cys Pro Phe Gly Phe Glu Gly Lys
65                  70                  75                  80

Asn Cys Glu Leu Asp Val Thr Cys Asn Ile Lys Asn Gly Arg Cys Glu
                85                  90                  95

Gln Phe Cys Lys Asn Ser Ala Asp Asn Lys Val Val Cys Ser Cys Thr
            100                 105                 110

Glu Gly Tyr Arg Leu Ala Glu Asn Gln Lys Ser Cys Glu Pro Ala Val
        115                 120                 125

Pro Phe Pro Cys Gly Arg Val Ser Val Ser Gln Thr Ser Lys Leu Thr
    130                 135                 140

Arg Ala Glu Thr Val Phe Pro Asp Val Asp Tyr Val Asn Ser Thr Glu
145                 150                 155                 160

Ala Glu Thr Ile Leu Asp Asn Ile Thr Gln Ser Thr Gln Ser Phe Asn
                165                 170                 175

Asp Phe Thr Arg Val Val Gly Gly Glu Asp Ala Lys Pro Gly Gln Phe
            180                 185                 190

Pro Trp Gln Val Val Leu Asn Gly Lys Val Asp Ala Phe Cys Gly Gly
        195                 200                 205

Ser Ile Val Asn Glu Lys Trp Ile Val Thr Ala Ala His Cys Val Glu
    210                 215                 220

Thr Gly Val Lys Ile Thr Val Val Ala Gly Glu His Asn Ile Glu Glu
225                 230                 235                 240

Thr Glu His Thr Glu Gln Lys Arg Asn Val Ile Arg Ile Ile Pro His
                245                 250                 255

His Asn Tyr Asn Ala Ala Ile Asn Lys Tyr Asn His Asp Ile Ala Leu
            260                 265                 270

Leu Glu Leu Asp Glu Pro Leu Val Leu Asn Ser Tyr Val Thr Pro Ile
        275                 280                 285

Cys Ile Ala Asp Lys Glu Tyr Thr Asn Ile Phe Leu Lys Phe Gly Ser
    290                 295                 300

Gly Tyr Val Ser Gly Trp Gly Arg Val Phe His Lys Gly Arg Ser Ala
305                 310                 315                 320

Leu Val Leu Gln Tyr Leu Arg Val Pro Leu Val Asp Arg Ala Thr Cys
                325                 330                 335

Leu Val Ser Thr Lys Phe Thr Ile Tyr Asn Asn Met Phe Cys Ala Gly
            340                 345                 350

Phe His Glu Gly Gly Arg Asp Ser Cys Gln Gly Asp Ser Gly Gly Pro
        355                 360                 365

His Val Thr Glu Val Glu Gly Thr Ser Phe Leu Thr Gly Ile Ile Ser
    370                 375                 380

Trp Gly Glu Glu Cys Ala Met Lys Gly Lys Tyr Gly Ile Tyr Thr Lys
385                 390                 395                 400
```

-continued

Val Ser Arg Tyr Val Asn Trp Ile Lys His Lys Thr Lys Leu Thr Pro
                405             410             415

Val Ser Gln Thr Ser Lys Leu Thr Arg Ala Glu Thr Val Phe Pro Asp
            420             425             430

Val Asp Ala His Lys Ser Glu Val Ala His Arg Phe Lys Asp Leu Gly
            435             440             445

Glu Glu Asn Phe Lys Ala Leu Val Leu Ile Ala Phe Ala Gln Tyr Leu
        450             455             460

Gln Gln Cys Pro Phe Glu Asp His Val Lys Leu Val Asn Glu Val Thr
465             470             475             480

Glu Phe Ala Lys Thr Cys Val Ala Asp Glu Ser Ala Glu Asn Cys Asp
                485             490             495

Lys Ser Leu His Thr Leu Phe Gly Asp Lys Leu Cys Thr Val Ala Thr
                500             505             510

Leu Arg Glu Thr Tyr Gly Glu Met Ala Asp Cys Cys Ala Lys Gln Glu
            515             520             525

Pro Glu Arg Asn Glu Cys Phe Leu Gln His Lys Asp Asp Asn Pro Asn
        530             535             540

Leu Pro Arg Leu Val Arg Pro Glu Val Asp Val Met Cys Thr Ala Phe
545             550             555             560

His Asp Asn Glu Glu Thr Phe Leu Lys Lys Tyr Leu Tyr Glu Ile Ala
            565             570             575

Arg Arg His Pro Tyr Phe Tyr Ala Pro Glu Leu Leu Phe Phe Ala Lys
            580             585             590

Arg Tyr Lys Ala Ala Phe Thr Glu Cys Cys Gln Ala Ala Asp Lys Ala
            595             600             605

Ala Cys Leu Leu Pro Lys Leu Asp Glu Leu Arg Asp Glu Gly Lys Ala
        610             615             620

Ser Ser Ala Lys Gln Arg Leu Lys Cys Ala Ser Leu Gln Lys Phe Gly
625             630             635             640

Glu Arg Ala Phe Lys Ala Trp Ala Val Ala Arg Leu Ser Gln Arg Phe
                645             650             655

Pro Lys Ala Glu Phe Ala Glu Val Ser Lys Leu Val Thr Asp Leu Thr
            660             665             670

Lys Val His Thr Glu Cys Cys His Gly Asp Leu Leu Glu Cys Ala Asp
            675             680             685

Asp Arg Ala Asp Leu Ala Lys Tyr Ile Cys Glu Asn Gln Asp Ser Ile
        690             695             700

Ser Ser Lys Leu Lys Glu Cys Cys Glu Lys Pro Leu Leu Glu Lys Ser
705             710             715             720

His Cys Ile Ala Glu Val Glu Asn Asp Glu Met Pro Ala Asp Leu Pro
                725             730             735

Ser Leu Ala Ala Asp Phe Val Glu Ser Lys Asp Val Cys Lys Asn Tyr
            740             745             750

Ala Glu Ala Lys Asp Val Phe Leu Gly Met Phe Leu Tyr Glu Tyr Ala
            755             760             765

Arg Arg His Pro Asp Tyr Ser Val Val Leu Leu Leu Arg Leu Ala Lys
            770             775             780

Thr Tyr Glu Thr Thr Leu Glu Lys Cys Cys Ala Ala Ala Asp Pro His
785             790             795             800

Glu Cys Tyr Ala Lys Val Phe Asp Glu Phe Lys Pro Leu Val Glu Glu
            805             810             815

-continued

```
Pro Gln Asn Leu Ile Lys Gln Asn Cys Glu Leu Phe Glu Gln Leu Gly
            820                 825                 830

Glu Tyr Lys Phe Gln Asn Ala Leu Leu Val Arg Tyr Thr Lys Lys Val
            835                 840                 845

Pro Gln Val Ser Thr Pro Thr Leu Val Glu Val Ser Arg Asn Leu Gly
            850                 855                 860

Lys Val Gly Ser Lys Cys Cys Lys His Pro Glu Ala Lys Arg Met Pro
865                 870                 875                 880

Cys Ala Glu Asp Tyr Leu Ser Val Val Leu Asn Gln Leu Cys Val Leu
                    885                 890                 895

His Glu Lys Thr Pro Val Ser Asp Arg Val Thr Lys Cys Cys Thr Glu
            900                 905                 910

Ser Leu Val Asn Arg Arg Pro Cys Phe Ser Ala Leu Glu Val Asp Glu
            915                 920                 925

Thr Tyr Val Pro Lys Glu Phe Asn Ala Glu Thr Phe Thr Phe His Ala
            930                 935                 940

Asp Ile Cys Thr Leu Ser Glu Lys Glu Arg Gln Ile Lys Lys Gln Thr
945                 950                 955                 960

Ala Leu Val Glu Leu Val Lys His Lys Pro Lys Ala Thr Lys Glu Gln
                    965                 970                 975

Leu Lys Ala Val Met Asp Asp Phe Ala Ala Phe Val Glu Lys Cys Cys
            980                 985                 990

Lys Ala Asp Asp Lys Glu Thr Cys Phe Ala Glu Glu Gly Lys Lys Leu
            995                 1000                1005

Val Ala Ala Ser Gln Ala Ala Leu Gly Leu
    1010                1015
```

```
<210> SEQ ID NO 16
<211> LENGTH: 231
<212> TYPE: PRT
<213> ORGANISM: Homo sapiens

<400> SEQUENCE: 16
```

```
Glu Pro Lys Ser Cys Asp Lys Thr His Thr Cys Pro Pro Cys Pro Ala
1               5                   10                  15

Pro Glu Leu Leu Gly Gly Pro Ser Val Phe Leu Phe Pro Pro Lys Pro
            20                  25                  30

Lys Asp Thr Leu Met Ile Ser Arg Thr Pro Glu Val Thr Cys Val Val
            35                  40                  45

Val Asp Val Ser His Glu Asp Pro Glu Val Lys Phe Asn Trp Tyr Val
    50                  55                  60

Asp Gly Val Glu Val His Asn Ala Lys Thr Lys Pro Arg Glu Glu Gln
65                  70                  75                  80

Tyr Asn Ser Thr Tyr Arg Val Val Ser Val Leu Thr Val Leu His Gln
                    85                  90                  95

Asp Trp Leu Asn Gly Lys Glu Tyr Lys Cys Lys Val Ser Asn Lys Ala
            100                 105                 110

Leu Pro Ala Pro Ile Glu Lys Thr Ile Ser Lys Ala Lys Gly Gln Pro
            115                 120                 125

Arg Glu Pro Gln Val Tyr Thr Leu Pro Pro Ser Arg Asp Glu Leu Thr
            130                 135                 140

Lys Asn Gln Val Ser Leu Thr Cys Leu Val Lys Gly Phe Tyr Pro Ser
145                 150                 155                 160

Asp Ile Ala Val Glu Trp Glu Ser Asn Gly Gln Pro Glu Asn Asn Tyr
                    165                 170                 175
```

Lys Thr Thr Pro Pro Val Leu Asp Ser Asp Gly Ser Phe Phe Leu Tyr
            180                 185                 190

Ser Lys Leu Thr Val Asp Lys Ser Arg Trp Gln Gln Gly Asn Val Phe
            195                 200                 205

Ser Cys Ser Val Met His Glu Ala Leu His Asn His Tyr Thr Gln Lys
            210                 215                 220

Ser Leu Ser Leu Ser Pro Gly
225                 230

<210> SEQ ID NO 17
<211> LENGTH: 226
<212> TYPE: PRT
<213> ORGANISM: Homo sapiens

<400> SEQUENCE: 17

Asp Lys Thr His Thr Cys Pro Pro Cys Pro Ala Pro Glu Leu Leu Gly
1                   5                   10                  15

Gly Pro Ser Val Phe Leu Phe Pro Pro Lys Pro Lys Asp Thr Leu Met
            20                  25                  30

Ile Ser Arg Thr Pro Glu Val Thr Cys Val Val Val Asp Val Ser His
            35                  40                  45

Glu Asp Pro Glu Val Lys Phe Asn Trp Tyr Val Asp Gly Val Glu Val
            50                  55                  60

His Asn Ala Lys Thr Lys Pro Arg Glu Glu Gln Tyr Asn Ser Thr Tyr
65                  70                  75                  80

Arg Val Val Ser Val Leu Thr Val Leu His Gln Asp Trp Leu Asn Gly
            85                  90                  95

Lys Glu Tyr Lys Cys Lys Val Ser Asn Lys Ala Leu Pro Ala Pro Ile
            100                 105                 110

Glu Lys Thr Ile Ser Lys Ala Lys Gly Gln Pro Arg Glu Pro Gln Val
            115                 120                 125

Tyr Thr Leu Pro Pro Ser Arg Asp Glu Leu Thr Lys Asn Gln Val Ser
            130                 135                 140

Leu Thr Cys Leu Val Lys Gly Phe Tyr Pro Ser Asp Ile Ala Val Glu
145                 150                 155                 160

Trp Glu Ser Asn Gly Gln Pro Glu Asn Asn Tyr Lys Thr Thr Pro Pro
            165                 170                 175

Val Leu Asp Ser Asp Gly Ser Phe Phe Leu Tyr Ser Lys Leu Thr Val
            180                 185                 190

Asp Lys Ser Arg Trp Gln Gln Gly Asn Val Phe Ser Cys Ser Val Met
            195                 200                 205

His Glu Ala Leu His Asn His Tyr Thr Gln Lys Ser Leu Ser Leu Ser
            210                 215                 220

Pro Gly
225

<210> SEQ ID NO 18
<211> LENGTH: 10
<212> TYPE: PRT
<213> ORGANISM: Artificial Sequence
<220> FEATURE:
<223> OTHER INFORMATION: CTP sequence

<400> SEQUENCE: 18

Ser Ser Ser Ser Lys Ala Pro Pro Pro Ser
1                   5                   10

```
<210> SEQ ID NO 19
<211> LENGTH: 32
<212> TYPE: PRT
<213> ORGANISM: Artificial Sequence
<220> FEATURE:
<223> OTHER INFORMATION: CTP sequence

<400> SEQUENCE: 19

Asp Pro Arg Phe Gln Asp Ser Ser Ser Ser Lys Ala Pro Pro Pro Ser
1               5                   10                  15

Leu Pro Ser Pro Ser Arg Leu Pro Gly Pro Ser Asp Thr Pro Ile Leu
            20                  25                  30

<210> SEQ ID NO 20
<211> LENGTH: 28
<212> TYPE: PRT
<213> ORGANISM: Artificial Sequence
<220> FEATURE:
<223> OTHER INFORMATION: CTP sequence

<400> SEQUENCE: 20

Ser Ser Ser Ser Lys Ala Pro Pro Pro Ser Leu Pro Ser Pro Ser Arg
1               5                   10                  15

Leu Pro Gly Pro Ser Asp Thr Pro Ile Leu Pro Gln
            20                  25

<210> SEQ ID NO 21
<211> LENGTH: 78
<212> TYPE: PRT
<213> ORGANISM: Artificial Sequence
<220> FEATURE:
<223> OTHER INFORMATION: XTEN artificial sequence

<400> SEQUENCE: 21

Gly Ala Pro Thr Ser Glu Ser Ala Thr Pro Glu Ser Gly Pro Gly Ser
1               5                   10                  15

Glu Pro Ala Thr Ser Gly Ser Glu Thr Pro Gly Thr Ser Glu Ser Ala
            20                  25                  30

Thr Pro Glu Ser Gly Pro Gly Ser Glu Pro Ala Thr Ser Gly Ser Glu
        35                  40                  45

Thr Pro Gly Thr Ser Glu Ser Ala Thr Pro Glu Ser Gly Pro Gly Thr
    50                  55                  60

Ser Thr Glu Pro Ser Glu Gly Ser Ala Pro Gly Ala Ser Ser
65                  70                  75

<210> SEQ ID NO 22
<211> LENGTH: 42
<212> TYPE: PRT
<213> ORGANISM: Artificial Sequence
<220> FEATURE:
<223> OTHER INFORMATION: XTEN artificial sequence

<400> SEQUENCE: 22

Gly Ala Pro Gly Ser Pro Ala Gly Ser Pro Thr Ser Thr Glu Glu Gly
1               5                   10                  15

Thr Ser Glu Ser Ala Thr Pro Glu Ser Gly Pro Gly Ser Glu Pro Ala
            20                  25                  30

Thr Ser Gly Ser Glu Thr Pro Ala Ser Ser
        35                  40

<210> SEQ ID NO 23
<211> LENGTH: 7
```

-continued

```
<212> TYPE: PRT
<213> ORGANISM: Artificial Sequence
<220> FEATURE:
<223> OTHER INFORMATION: Linker

<400> SEQUENCE: 23

Gly Gly Gly Gly Gly Gly Val
1               5
```